(12) United States Patent
Kato et al.

(10) Patent No.: US 10,131,877 B2
(45) Date of Patent: Nov. 20, 2018

(54) DIFFERENTIATION-INDUCING CULTURE MEDIUM ADDITIVE AND USE THEREOF

(71) Applicant: Two Cells Co., Ltd., Hiroshima, Hiroshima (JP)

(72) Inventors: Yukio Kato, Hiroshima (JP); Jin Chang Shao, Hiroshima (JP); Koichiro Tsuji, Hiroshima (JP)

(73) Assignee: TWO CELLS Co., Ltd., Hiroshima, Hiroshima (JP)

(*) Notice: Subject to any disclaimer, the term of this patent is extended or adjusted under 35 U.S.C. 154(b) by 0 days.

(21) Appl. No.: 14/885,134

(22) Filed: Oct. 16, 2015

(65) Prior Publication Data
US 2016/0032247 A1 Feb. 4, 2016

Related U.S. Application Data

(62) Division of application No. 13/127,774, filed as application No. PCT/JP2009/005573 on Oct. 22, 2009, now abandoned.

(30) Foreign Application Priority Data

Nov. 11, 2008 (JP) ................................ 2008-289146

(51) Int. Cl.
*C12N 5/077* (2010.01)
(52) U.S. Cl.
CPC ........ *C12N 5/0654* (2013.01); *C12N 2500/25* (2013.01); *C12N 2500/42* (2013.01); *C12N 2500/90* (2013.01); *C12N 2501/11* (2013.01); *C12N 2501/115* (2013.01); *C12N 2501/12* (2013.01); *C12N 2501/135* (2013.01); *C12N 2501/15* (2013.01); *C12N 2501/39* (2013.01); *C12N 2501/40* (2013.01); *C12N 2506/1353* (2013.01)

(58) Field of Classification Search
CPC A61K 35/32; A61K 38/1875; C12N 2501/11; C12N 5/0623; A61L 27/3834; A61L 2300/414; G01N 33/5073
See application file for complete search history.

(56) References Cited

U.S. PATENT DOCUMENTS

| | | |
|---|---|---|
| 6,617,159 B1 | 9/2003 | Cancedda et al. |
| 7,109,032 B2 | 9/2006 | Cancedda et al. |
| 7,169,610 B2 | 1/2007 | Brown |
| 2003/0143737 A1 | 7/2003 | Morrison et al. |
| 2003/0211604 A1 | 11/2003 | Brown |
| 2005/0013804 A1 | 1/2005 | Kato et al. |
| 2005/0032122 A1 | 2/2005 | Hwang et al. |
| 2005/0090002 A1 | 4/2005 | Cancedda et al. |
| 2005/0132426 A1 | 6/2005 | Morrison et al. |
| 2005/0265980 A1 | 12/2005 | Xu et al. |
| 2005/0272152 A1 | 12/2005 | Xu et al. |
| 2006/0216821 A1 | 9/2006 | Totey et al. |
| 2007/0275463 A1 | 11/2007 | Brown |
| 2009/0202654 A1 | 8/2009 | Nixon |
| 2010/0279412 A1* | 11/2010 | Kato ................ C12N 5/0031 435/384 |

FOREIGN PATENT DOCUMENTS

| | | |
|---|---|---|
| EP | 0 274 445 B1 | 7/1993 |
| EP | 1 988 159 A1 | 11/2008 |
| JP | 08-308561 | 11/1996 |
| JP | 09-191874 | 7/1997 |
| JP | 2002-529071 | 9/2002 |
| JP | 2003-516141 | 5/2003 |
| JP | 2005-515777 | 6/2005 |
| JP | 2007-000077 A | 1/2007 |
| JP | 2007-536935 A | 12/2007 |
| KR | 2008-0091809 | 10/2008 |
| WO | WO 97/34614 | 9/1997 |
| WO | WO 1999/047163 A2 | 9/1999 |
| WO | WO 03/104442 | 12/2003 |
| WO | WO 2004/069172 A2 | 8/2004 |

(Continued)

OTHER PUBLICATIONS

Peter et al. Osteoblastic phenotype of rat marrow stromal cells cultured in the presence of dexamethasone, beta-glycerolphosphate, and L-ascorbic acid. Journal of Cellular Biochemistry. 1998;71:55-62.*
Wiesmann et al. Decreased CD90 expression in human mesenchymal stem cells by applying mechanical stimulation. Head Face Med. 2006;2(8):1-6.*
Office Action for corresponding U.S. Appl. No. 13/127,774 dated Oct. 2, 2012.
Office Action for co-pending U.S. Appl. No. 13/127,774 dated Feb. 27, 2013.
Advisory Action for co-pending U.S. Appl. No. 13/127,774 dated May 10, 2013.
Office Action for co-pending U.S. Appl. No. 13/127,774 dated Dec. 6, 2013.

(Continued)

*Primary Examiner* — Lynn Y Fan
(74) *Attorney, Agent, or Firm* — Renner, Otto, Boisselle & Sklar, LLP

(57) ABSTRACT

Provided is a differentiation-inducing culture medium additive for inducing bone differentiation of at least one type of cell selected from the group consisting of a stem cell, a dental pulp cell, a periodontal ligament cell, a placenta, an amnion, and a fibroblast under a serum-free condition, and a use of the differentiation-inducing culture medium additive. The differentiation-inducing culture medium additive of the present invention for inducing differentiation of a stem cell under a serum-free condition at least contains at least one growth factor selected from the group consisting of EGF, FGF, and PDGF; dexamethasone; and β-glycerophosphate. The differentiation-inducing culture medium additive of the present invention does not require ascorbic acid 2-phosphate and ITS, which are normally essential for bone differentiation. Further, bone differentiation can be promoted by adding phospholipid.

6 Claims, 4 Drawing Sheets

(56) References Cited

FOREIGN PATENT DOCUMENTS

| WO | WO 2007/080919 A1 | | 7/2007 | |
|---|---|---|---|---|
| WO | WO2007080919 | * | 7/2007 | ............... C12N 5/06 |
| WO | WO 2009/114860 A2 | | 9/2009 | |

OTHER PUBLICATIONS

Final Office Action for co-pending U.S. Appl. No. 13/127,774 dated May 8, 2014.
Advisory Action from co-pending U.S. Appl. No. 13/127,774 dated Jul. 31, 2014.
Office Action for co-pending U.S. Appl. No. 13/127,774 dated Dec. 19, 2014.
Final Office Action for co-pending U.S. Appl. No. 13/127,774 dated Jul. 17, 2015.
Advisory Action for co-pending U.S. Appl. No. 13/127,774 dated Sep. 29, 2015.
Valta et al., "Regulation of Osteoblast Differentiation: A Novel Function for Fibroblast Growth Factor 8", Endocrinology, May 2006, 147(5), pp. 2171-2182.
Broedel, Jr. et al., "The Case for Serum-Free Media", BioProcess International, Feb. 2003, pp. 56-58.
Singh et al., "Parathyroid Hormone Stimulates Phosphatidylethanolamine Hydrolysis by Phospholipase D in Osteoblastic Cells", Lipids, Nov. 2005, 40(11), pp. 1135-1140.
Pasco et al., "Antioxidant Vitamin Supplements and Markers of Bone Turnover in a Community Sample of Nonsmoking Women", Journal of Women's Health, 2006, 15(3), pp. 295-300.
GIBCO Invitrogen Cell Culture. StemPro Osteogenesis Differentiation Kit. 2008.
Peter et al., "Osteoblastic Phenotype of Rat Marrow Stromal Cells Cultured in the Presence of Dexamethasone, ß-Glycerolphosphate, and L-ascorbic acid", Journal of Cellular Biochemistry, 71, 1998; pp. 55-62.
Shioi et al., "ß-Glycerophosphate Accelerates Calcification in cultured Bovine Vascular Smooth Muscle Cells", Arteriosclerosis, Thrombosis, and Vascular Biology, 1995; 15:2003-2009.
Djouad et al., "Immunosuppressive effect of mesenchymal stem cells favors tumor growth in allogeneic animals", Blood 102, pp. 3837-8344, 2003.
Office Action for copending U.S. Appl. No. 13/583,150 dated Jul. 22, 2013.
Restriction Requirement for corresponding U.S. Appl. No. 12/160,481 dated Oct. 29, 2010.
Restriction Requirement for corresponding U.S. Appl. No. 12/160,481 dated Feb. 2, 2011.
Advisory Action for corresponding U.S. Appl. No. 12/160,481 dated Dec. 1, 2011.
Advisory Action for corresponding U.S. Appl. No. 12/160,481 dated Dec. 12, 2012.
International Search Report for corresponding International Application No. PCT/JP2009/005573 dated Dec. 15, 2009.
Form PCT/ISA/237 for International Application No. PCT/JP2009/005573 dated Dec. 15, 2009.
Kratchmarova et al., "Mechanism of Divergent Growth Factor Effects in Mesenchymal Stem Cell Differentiation", Science (2005), vol. 308, p. 1472-1477.
Campagnoli et al., "Identification of mesenchymal stem/progenitor cells in human first-trimester fetal blood, liver, and bone marrow", Blood (2001), vol. 98, No. 8, p. 2396-2402.
Misawa et al., "Bone regeneration using embryonic stem cells" ("Haisei Kansaibo o Mochiita Hone Saisei"), Organ Biology (2005), vol. 12, No. 4, pp. 281-289 with machine translation.
Supplementary European Search Report for corresponding European Application No. EP 09 82 5870 dated Mar. 21, 2012.
Kotev-Emeth et al., "Establishment of a Rat Long-Term Culture Expressing the Osteogenic Phenotype: Dependence on Dexamethasone and FGF-2", Connective Tissue Research, 2002, vol. 43, pp. 606-612.

Maegawa et al., "Enhancement of osteoblastic differentiation of mesenchymal stromal cells cultured by selective combination of bone morphogenetic protein-2 (BMP-2) and fibroblast growth factor-2 (FGF-2)", Journal of tissue engineering and regenerative medicine, 2007, vol. 1, pp. 306-313.
Chaudhary et al., "Differential growth factor control of bone formation through osteoprogenitor differentiation", Bone, 2004, vol. 34, pp. 402-411.
Frank et al., "Real-Time Quantitative RT-PCR Analysis of Human Bone Marrow Stromal Cells During Osteogenic Differentiation in Vitro", Journal of Cellular Biochemistry, 2002, vol. 85, pp. 737-746.
Friedman et al., "Osteogenic Differentiation of Human Mesenchymal Stem Cells is Regulated by Bone Morphogenetic Protein-6", Journal of Cellular Biochemistry, 2006, vol. 98, pp. 538-554.
International Search Report for corresponding International Application No. PCT/JP2011/055683 dated Apr. 5, 2011.
Form PCT/ISA/237 for corresponding International Application No. PCT/JP2011/055683 dated Apr. 5, 2011.
Y Kato, "Development of Serum-free Medium for Human Mesenchymal Stem Cells", Iryokiki Forum (Medical Equipment Forum), 33-35, 2007 and full English translation.
Armand Keating, "How Do Mesenchymal Stromal Cells Suppress T Cells?", Cell Stem Cell, 2, pp. 106-108, 2008.
Corcione et al., "Human mesenchymal stem cells modulates B-cell functions", Blood 107, pp. 367-372, 2006.
Ramasamy et al., "Mesenchymal Stem Cells Inhibit Dendritic Cell Differentiation and Function by Preventing Entry Into the Cell Cycle", Transplantation 83, No. 1, pp. 71-76, 2007.
Aggarwal et al., "Human mesenchymal stem cells modulate allogeneic immune cell responses", Blood 105, pp. 1815-1822, 2005.
Le Blanc et al., "Immunomodulation by mesenchymal stem cells and clinical experience", Journal of Internal Medicine, 262, pp. 3837-3844, 2003.
Y. Kato, "Active Stemness Molecular Mechanism of Mesenchymal Stem Cells in Serum-free Medium: Diversion from serum regenerative medicine to serum-free regenerative medicine", Research Council Meeting of Japan Society of Plastic and Reconstructive Surgery, 2009, vol. $18^{th}$, pp. 54-55 and full English translation.
Sawada et al., "Gene Expression Changes in Human Bone-marrow Derived Mesenchymal Stem Cells during the in vitro Culture-Influence of Serum-free Medium", Regenerative Medicine, 2009, vol. 8, No. suppl, p. 248 and full English translation.
Doucet et al., "Platelet Lysates Promote Mesenchymal Stem Cell Expansion: A Safety Substitute for Animal Serum in Cell-Based Therapy Applications", Journal of Cellular Physiology, 2005, vol. 205, pp. 228-236.
Sotiropoulou et al., "Characterization of the Optimal Culture Conditions for Clinical Scale Production of Human Mesenchymal Stem Cells", Stem Cells, 2006, vol. 24, pp. 462-471.
Di Nicola et al., "Human bone marrow stromal cells suppress T-lymphocyte proliferation induced by cellular or nonspecific mitogenic stimuli", Blood, 2002, vol. 99, No. 10, pp. 3838-3843.
Chiyo Hori et al.; "Induction of lithium ion of multiplication of mouse mammary epithelium in culture"; Proc. Natl Acad. Sci. USA; vol. 76, No. 6; pp. 2823-2827; Jun. 1979.
Yoshiro Saito et al., "III-14 Research on Effect of Essential Micronutrient Selenium on Cell Survival"; Proceedings of the Japanese Conference on the Biochemistry of Lipids; vol. 45; pp. 262-265; 2003. (Includes partial English translation).
International Search Report for corresponding Application No. PCT/JP2007/050232 dated Mar. 20, 2007.
Hideki Yamaji et al.; "Promoting effect of phospholipid on proliferation of CHO cells in serum free culturing"; Abstracts of Presentations for the Muroran Meeting of the Society of Chemical Engineering, Japan, at Muroran Institute of Technology, Aug. 6-7, 1998; p. 140. (Includes partial English translation).
Regina Labitzke et al.; "A serum-free medium formulation supporting growth of human umbilical cord vein endothelial cells in long-term cultivation"; Cytotechnology, 35; pp. 87-92; 2001.
Emily Shacter; "Serum-free medium for growth factor-dependent and—independent plasmacytomas and hybridomas"; Journal of Immunological Methods, 99; pp. 259-270; 2001.

(56) References Cited

OTHER PUBLICATIONS

Kentaro Sakai et al.; "Use of Nonionic Surfactants for Effective Supply of Phosphatidic Acid in Serum-Free Culture of Chinese Hamster Ovary Cells"; Journal of Bioscience and Bioengineering; vol. 92, No. 3; pp. 256-261; 2001.
Ben J. Walthall et al.; "Multiplication of Human Diploid Fibroblasts in a Synthetic Medium Supplemented with EGF; Insulin, and Dexamethoasone"; Experimental Cell Research, 134; pp. 303-311; 1981.
European Search Report for corresponding Application No. 07706579.5 dated Apr. 2, 2009.
Forte Giancarlo et al.; "Hepatocyte growth factor effects on mesenchymal stem cells: proliferation, migration, and differentiation"; Stem Cells; Jan. 2006, vol. 24, No. 1; pp. 23-33.
Korean Office Action for corresponding Korean Application No. 10-2008-7019812 dated Oct. 11, 2010 (with English translation).
Sandstorm et al.; "Review: Serum-Free Media for Cultures of Primitive and Mature Hematopoietic Cells"; Biotechnology and Bioengineering, 1994, vol. 43; pp. 706-733.
Neuss et al., "Functional Expression of HGF and HFG Receptoric-met in Adult Human Mesenchymal Stem Cells Suggests a Role in Cell Mobilization, Tissue Repair, and Wound Healing", Stem Cells, 2004, 22, pp. 405-414.
U.S. Office Action dated Mar. 30, 2011 for corresponding U.S. Appl. No. 12/160,481.
U.S. Office Action dated Sep. 15, 2011 for corresponding U.S. Appl. No. 12/160,481.
U.S. Office Action dated Jun. 5, 2012 for corresponding U.S. Appl. No. 12/160,481.
U.S. Office Action dated Oct. 9, 2012 for corresponding U.S. Appl. No. 12/160,481.
Summons to Attend Oral Proceedings Pursuant to Rule 115(1) EPC for corresponding Application No. EP 07706579.5 dated Oct. 25, 2012.
Lee et al., Blood vol. 3, Mar. 1, 2004, pp. 1669-1675.
Office Action corresponding to U.S. Appl. No. 12/160,481 dated Mar. 29, 2013.
Office Action corresponding to U.S. Appl. No. 13/583,150 dated Apr. 11, 2013.
Office Action dated Jul. 22, 2013 in copending U.S. Appl. No. 13/583,150.
Burns et al., "Tumorigenic Heterogeneity in Cancer Stem Cells Evolved from Long-term Cultures of Telomerase-Immortalized Human Mesenchymal Stem Cells", Cancer Research 65(8): pp. 3126-3135, Apr. 15, 2005.
Clyman et al., "Integrin receptors on aortic smooth muscle cells mediate adhesion to fibronectin, laminin, and collagen", Circulation Research, vol. 67, No. 1, pp. 175-186, Jul. 1990.
Kao et al., "TrypZean™: Recombinant Bovine Trypsin Expressed in Corn—A Non-animal Alternative", SIGMA® Technical Articles, available online, two pages, published Jan. 2004.

Extended European Search Report dated Aug. 2, 2013 in European Application No. 11753445.3.
Office Action for corresponding U.S. Appl. No. 12/160,481 dated Oct. 21, 2013.
Gregory et al., Journal of Biological Chemistry, vol. 280: "Dkk-1-derived Synthetic Peptides and Lithium Chloride for the Control and Recovery of Adult Stem Cells from Bone Marrow", pp. 2309-2323, dated Jan. 21, 2005.
Lee et al., "Tumorigenesis Study of Canine Adipose Derived-mesenchymal Stem Cell", Journal of Toxicology and Public Health, Sep. 21, 2007, pp. 271-278, vol. 23, No. 3, with English translation thereof.
Yañez et al., "Adipose Tissue-Derived Mesenchymal Stem Cells Have In Vivo Immunosuppressive Properties Applicable for the Control of the Graft-Versus-Host Disease", Stem Cells, Jul. 27, 2006, pp. 2582-2591, vol. 24, AlphaMed Press.
Office Action for corresponding Korean Application No. 10-2012-7026184, dated Nov. 29, 2013, with English translation thereof.
Office Action for co-pending U.S. Appl. No. 13/583,150, dated Dec. 18, 2013.
Advisory Action for co-pending U.S. Appl. No. 12/160,481, dated Jan. 7, 2014.
Advisory Action for corresponding U.S. Appl. No. 13/583,150 dated Mar. 3, 2014.
Office Action for related U.S. Appl. No. 12/160,481 dated Jun. 4, 2014.
Final Office Action for related U.S. Appl. No. 12/160,481 dated Sep. 16, 2014.
Office Action for co-pending U.S. Appl. No. 13/583,150, dated Jan. 26, 2015.
Chen et al. ""Extracellular matrix made by bone marrow cells facilitates expansion of marrow-derived mesenchymal progenitor cells and prevents their differentiation into osteoblasts"", Journal of Bone and Mineral Research 22(12): 1943-1956, 2007.
Advisory Action for co-pending U.S. Appl. No. 12/160,481, dated Jan. 22, 2015.
Final Office Action for co-pending U.S. Appl. No. 13/583,150 dated Jun. 26, 2015.
Non-Final Office Action for co-pending U.S. Appl. No. 13/583,150 dated Sep. 9, 2015.
Stem Cell Research "The next revolution in MSC culture: Stempro MSC SFM serum-free human mesenchymal stem cell culture medium", Invitrogen, available from company webpage <www.invitrogen.com>, copyright 2008.
Office Action for related U.S. Appl. No. 14/725,073, dated Jun. 7, 2017.
Office Action for related U.S. Appl. No. 14/725,073, dated Nov. 2, 2017.
Office Action for related U.S. Appl. No. 14/725,073, dated Jun. 4, 2018.

\* cited by examiner

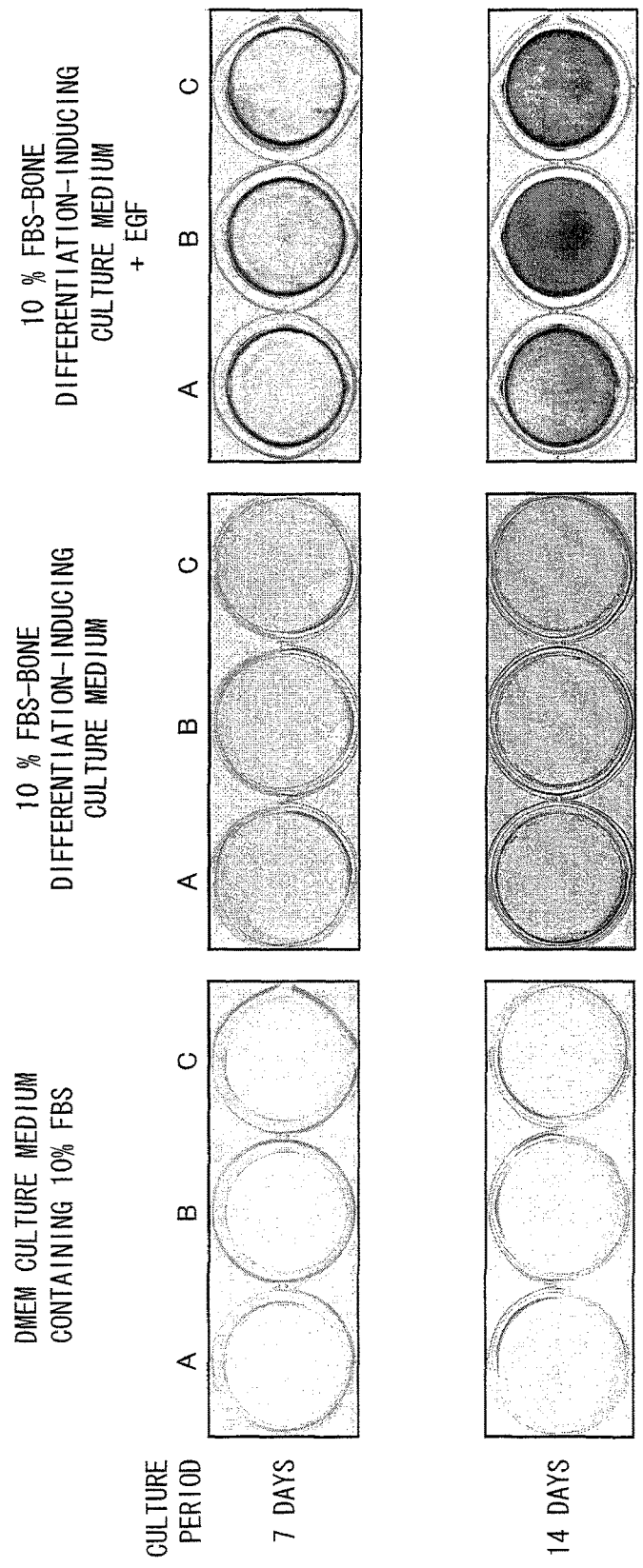

FIG. 4

| 4TH DAY | CELL PROLIFERATED AND CULTURED BY USE OF DMEM CULTURE MEDIUM CONTAINING 10% FBS ||| CELL PROLIFERATED AND CULTURED BY USE OF SERUM-FREE PROLIFERATION CULTURE MEDIUM (STK2 CULTURE MEDIUM) |||
|---|---|---|---|---|---|---|
| DIFFERENTIATION CULTURE MEDIUM TYPE/CELL LINE | CELL LINE K | CELL LINE L | CELL LINE M | CELL LINE K | CELL LINE L | CELL LINE M |
| 1. 10 % FBS-BONE DIFFERENTIATION-INDUCING CULTURE MEDIUM |  |  |  |  |  |  |
| 2. SERUM-FREE BONE DIFFERENTIATION-INDUCING CULTURE MEDIUM (STK3 CULTURE MEDIUM) |  |  |  |  |  |  |

| 7TH DAY | CELL PROLIFERATED AND CULTURED BY USE OF DMEM CULTURE MEDIUM CONTAINING 10% FBS ||| CELL PROLIFERATED AND CULTURED BY USE OF SERUM-FREE PROLIFERATION CULTURE MEDIUM (STK2 CULTURE MEDIUM) |||
|---|---|---|---|---|---|---|
| DIFFERENTIATION CULTURE MEDIUM TYPE/CELL LINE | CELL LINE K | CELL LINE L | CELL LINE M | CELL LINE K | CELL LINE L | CELL LINE M |
| 1. 10 % FBS-BONE DIFFERENTIATION-INDUCING CULTURE MEDIUM |  |  |  |  |  |  |
| 2. SERUM-FREE BONE DIFFERENTIATION-INDUCING CULTURE MEDIUM (STK3 CULTURE MEDIUM) |  |  |  |  |  |  |

| 14TH DAY | CELL PROLIFERATED AND CULTURED BY USE OF DMEM CULTURE MEDIUM CONTAINING 10% FBS ||| CELL PROLIFERATED AND CULTURED BY USE OF SERUM-FREE PROLIFERATION CULTURE MEDIUM (STK2 CULTURE MEDIUM) |||
|---|---|---|---|---|---|---|
| DIFFERENTIATION CULTURE MEDIUM TYPE/CELL LINE | CELL LINE K | CELL LINE L | CELL LINE M | CELL LINE K | CELL LINE L | CELL LINE M |
| 1. 10 % FBS-BONE DIFFERENTIATION-INDUCING CULTURE MEDIUM |  |  |  |  |  |  |
| 2. SERUM-FREE BONE DIFFERENTIATION-INDUCING CULTURE MEDIUM (STK3 CULTURE MEDIUM) |  |  |  |  |  |  |

| 21ST DAY | CELL PROLIFERATED AND CULTURED BY USE OF DMEM CULTURE MEDIUM CONTAINING 10% FBS ||| CELL PROLIFERATED AND CULTURED BY USE OF SERUM-FREE PROLIFERATION CULTURE MEDIUM (STK2 CULTURE MEDIUM) |||
|---|---|---|---|---|---|---|
| DIFFERENTIATION CULTURE MEDIUM TYPE/CELL LINE | CELL LINE K | CELL LINE L | CELL LINE M | CELL LINE K | CELL LINE L | CELL LINE M |
| 1. 10 % FBS-BONE DIFFERENTIATION-INDUCING CULTURE MEDIUM |  |  |  |  |  |  |
| 2. SERUM-FREE BONE DIFFERENTIATION-INDUCING CULTURE MEDIUM (STK3 CULTURE MEDIUM) |  |  |  |  |  |  |

DIFFERENTIATION-INDUCING CULTURE MEDIUM ADDITIVE AND USE THEREOF

CROSS-REFERENCE TO RELATED APPLICATION

The present application is a Divisional application of Ser. No. 13/127,774 filed on May 5, 2011 which is a National Phase Application based off of international application no. PCT/JP2009/005573 filed on Oct. 22, 2009 and claims priority to Japanese application no. 2008-289146 filed on Nov. 11, 2008.

TECHNICAL FIELD

The present invention relates to a differentiation-inducing culture medium additive and a use thereof. More specifically, the present invention relates to a differentiation-inducing culture medium additive for inducing bone differentiation of at least one type of cell selected from the group consisting of a stem cell, a dental pulp cell, a periodontal ligament cell, a placenta, an amnion, and a fibroblast under a serum-free condition, and to a use of the differentiation-inducing culture medium additive.

BACKGROUND ART

A stem cell is a cell having a self-reproducing potential and a differentiation potential. For example, an embryonic stem cell (an ES cell), an induced pluripotent stem cell (an iPS cell), and a somatic stem cell are known as stem cells. Examples of the somatic stem cell include: a hematopoietic stem cell, a neural stem cell, and a mesenchymal stem cell. Each of the ES cell and the iPS cell has a pluriopotency to differentiate into any tissue. The hematopoietic stem cell has a potential to differentiate into a blood cell. The neural stem cell has a potential to differentiate into a nerve cell. The mesenchymal stem cell is present in tissues of bone marrow or the like, and is known as a stem cell having a pluriopotency to differentiate into an adipose cell, a bone cell, a chondrocyte, or the like.

Of these stem cells, for example, the mesenchymal stem cell is currently used as a cell for transplantation in a regenerative medicine field. The mesenchymal stem cell is adapted to various diseases such as a bone defect, a cartilage defect, a periodontal disease, a myocardial infarction, a refractory dermatosis, osteoporosis, osteoarthrosis, a spinal cord injury, hematopoietic support, and antirejection in organ transplantation. It is expected that in the future, the mesenchymal stem cell will be adapted to more and more diseases (e.g., a cerebral infarction, arteriosclerosis obliterans, a kidney disorder, etc.).

Currently, a culture medium to which an animal serum (generally 10 to 15% fetal bovine serum) is added is extensively used as a culture medium for inducing differentiation of the stem cells into various functional cells. Such a serum is used as a nutrient source for promoting in vitro cell growth and/or proliferation, or a supply source of a biologically active substance such as hormone.

However, a serum is very expensive, and components thereof differ for each lot because the serum is a natural product. This is highly likely to cause variation in promotion effect of cell differentiation. Moreover, cultured cells need to be purified so that serum-derived proteins or the like are removed from the cultured cells. This requires a complicated process. Furthermore, there is a risk that cultured cells may be infected with an unknown pathogen (such as a virus or pathogenic prion) that is included in the serum. Further, for example, in case of inducing differentiation of a mesenchymal stem cell by use of a culture medium containing a serum, the serum may contain a component inhibiting bone differentiation of the mesenchymal stem cell. This may cause bone differentiation of the mesenchymal stem cell to be carried out with lower efficiency. In view of the circumstances, a technique which allows inducing differentiation of the above-mentioned stem cells under a serum-free condition is essential to realization and spread of regenerative medicine.

For example, in order to induce differentiation of a mesenchymal stem cell into an osteoblast cell, a method is known for carrying out bone differentiation by use of a reduced amount of serum. For example, a method is disclosed for inducing differentiation of a mesenchymal stem cell into an osteoplastic cell by adding an epidermal growth factor (EGF) to a culture medium in which an amount of fetal bovine serum is reduced to 1% (see Non Patent Literature 1).

Further, a technique is also known in which a composition containing a specific growth factor and a phospholipid is added to a basal medium, so as to induce a cell, which has been obtained by culturing a mesenchymal stem cell under a serum-free condition, to differentiate into an osteoblast cell or an adipose cell with the use of a serum-containing culture medium (see Patent Literature 1).

CITATION LIST

Patent Literature 1
International Publication No. 2007/080919A1 (Publication Date: Jul. 19, 2007)
Non Patent Literature 1
SCIENCE, 308, 1472-1477, 2005.

SUMMARY OF INVENTION

Technical Problem

However, according to the arrangement of Patent Literature 1, differentiation of a mesenchymal stem cell cannot be induced under a serum-free condition although a mesenchymal stem cell can be cultured under a serum-free condition.

Further, according to the arrangement of Non-Patent Literature 1, differentiation is induced in a serum-containing culture medium although a used amount of serum is reduced. This causes problems arising from serum such as variations in differentiation promotion effect, a complicated purification process, infection of cultured cells, and high cost of differentiation induction. Meanwhile, no finding has been made as for a method for inducing differentiation of a mesenchymal stem cell into an osteoblast cell under a serum-free condition.

Similarly, almost no finding has been made as for a method for inducing other stem cells under a serum-free condition. For example, in order to prepare a serum-free culture medium used for differentiation induction of an ES cell into a nerve cell under a serum-free condition, it is necessary to add, to a basal medium, expensive additives, i.e., commercially available N2 additive and B27 additive (produced by Gibco BRL). That is, although it is possible to induce differentiation under a serum-free condition, there is a problem that the expensive additives must be added instead of serum.

The present invention was attained in view of the above problems, and an object of the present invention is to provide a differentiation-inducing culture medium additive for efficiently inducing bone differentiation of at least one type of cell selected from the group consisting of a stem cell, a dental pulp cell, a periodontal ligament cell, a placenta, an amnion, and a fibroblast under a serum-free condition at low cost, and a use of the differentiation-inducing culture medium additive.

Solution to Problem

A differentiation-inducing culture medium additive of the present invention for inducing bone differentiation of at least one type of cell selected from the group consisting of a stem cell, a dental pulp cell, a periodontal ligament cell, a placenta, an amnion, and a fibroblast under a serum-free condition, at least contains: at least one growth factor selected from the group consisting of EGF, FGF, and PDGF; dexamethasone; and β-glycerophosphate.

According to the arrangement, the growth factor has a function of promoting a bone differentiation program of at least one type of cell selected from the group consisting of a stem cell, a dental pulp cell, a periodontal ligament cell, a placenta, an amnion, and a fibroblast (these cells are hereinafter collectively referred to as "target cell"), and dexamethasone has a function of promoting survival and differentiation of cells, and β-glycerophosphate has a function of supplying phosphoric acid and promoting calcification. Accordingly, it is possible to efficiently induce bone differentiation of a target cell under a serum-free condition by adding the differentiation-inducing culture medium additive of the present invention to a basal medium.

Consequently, uniform and stable differentiation promotion effect can be obtained. Further, there is no need to perform purification for removing serum-derived proteins or the like from cultured cells. Further, it is possible to prevent cultured cells from being infected with an unknown pathogen that is included in the serum. Further, there is no need to use expensive serum. This allows the differentiation induction to be performed at low cost. Further, recombinant human insulin, transferrin, selenate, and ascorbic acid, which have been conventionally considered as being essential for bone differentiation induction, need not necessarily to be added. This makes it possible to provide a differentiation-inducing culture medium additive at lower cost.

The differentiation-inducing culture medium additive of the present invention preferably further contains at least one phospholipid. Further, the at least one phospholipid is preferably selected from the group consisting of phosphatidic acid, lysophosphatidic acid, phosphatidylinositol, phosphatidylserine, phosphatidylethanolamine, phosphatidyl choline, and phosphatidylglycerol.

According to the arrangement, differentiation of a target cell can be induced due to the functions of the growth factor, dexamethasone, and β-glycerophosphate, and a signal transduction system for inducing bone differentiation of the target cell is activated due to the function of the at least one phospholipid. This further promote the bone differentiation. Accordingly, it is possible to more efficiently induce bone differentiation of the target cell, thereby shortening a period of time required for the bone differentiation induction. As a result, it is possible to reduce cost for the bone differentiation induction.

The differentiation-inducing culture medium additive of the present invention preferably further contains an oxidation inhibitor. The oxidation inhibitor is preferably DL-α-tocopherol acetate (vitamin E).

According to the arrangement, it is possible to prevent degradation of the phospholipid. Accordingly, it is possible to more efficiently differentiate the target cell into a bone.

Further, the differentiation-inducing culture medium additive is preferably used in inducing bone differentiation of a mesenchymal stem cell which is used as the stem cell.

According to the arrangement, the growth factor has a function of promoting a bone differentiation program, dexamethasone has a function of inducing a bone morphogenetic protein (BMP), and β-glycerophosphate is converted into inorganic phosphoric acid by alkaline phosphatase so as to supply phosphoric acid, and has a function of promoting calcification. Accordingly, it is possible to efficiently induce differentiation of a mesenchymal stem cell into an osteoblast cell under a serum-free condition by adding the differentiation-inducing culture medium additive of the present invention to a basal medium. Consequently, uniform and stable differentiation promotion effect can be obtained. Further, in a case where the differentiation-inducing culture medium additive further contains at least one phospholipid, a signal transduction system for inducing bone differentiation of a mesenchymal stem cell is activated. This further promotes the bone differentiation. Accordingly, it is possible to more efficiently induce differentiation of the mesenchymal stem cell into an osteoblast cell, thereby shortening a period of time required for the bone differentiation induction. As a result, it is possible to reduce cost for the bone differentiation induction.

A culture medium of the present invention for inducing bone differentiation of at least one type of cell selected from the group consisting of a stem cell, a dental pulp cell, a periodontal ligament cell, a placenta, an amnion, and a fibroblast under a serum-free condition, contains: components constituting the differentiation-inducing culture medium additive of the present invention; and a basal medium, and the culture medium contains no serum.

The culture medium is preferably used in inducing bone differentiation of a mesenchymal stem cell which is used as the stem cell.

A culture method of the present invention for inducing bone differentiation of at least one type of cell selected from the group consisting of a stem cell, a dental pulp cell, a periodontal ligament cell, a placenta, an amnion, and a fibroblast under a serum-free condition, includes the step of: differentiating at least one type of cell selected from the group consisting of the stem cell, the dental pulp cell, the periodontal ligament cell, the placenta, the amnion, and the fibroblast in the culture medium.

The culture method is preferably used in inducing bone differentiation of a mesenchymal stem cell which is used as the stem cell.

A kit of the present invention for inducing bone differentiation of at least one type of cell selected from the group consisting of a stem cell, a dental pulp cell, a periodontal ligament cell, a placenta, an amnion, and a fibroblast under a serum-free condition, includes: components constituting the differentiation-inducing culture medium additive of the present invention.

The kit is preferably used in inducing bone differentiation of a mesenchymal stem cell which is used as the stem cell.

As described above, the differentiation-inducing culture medium additive of the present invention at least contains at least one growth factor selected from the group consisting of EGF, FGF, and PDGF; dexamethasone; and β-glycerophosphate. This makes it possible to induce bone differentiation of a target cell under a serum-free condition. Further, in a case where the differentiation-inducing culture medium additive contains at least one phospholipid, it is possible to further promote bone differentiation of the target cell under a serum-free condition.

Accordingly, it is possible to efficiently induce bone differentiation of a target cell by culturing the target cell in the culture medium. Further, use of the kit makes it possible to easily perform bone differentiation of a target cell, which has been conventionally difficult under a serum-free condition.

Further, in a case where a mesenchymal stem cell is used as the stem cell, it is possible to efficiently induce differentiation of the mesenchymal stem cell into an osteoblast cell. Further, use of the kit makes it possible to easily perform differentiation of a mesenchymal stem cell into an osteoblast cell, which has been conventionally difficult under a serum-free condition.

The culture method for inducing bone differentiation of at least one type of cell selected from the group consisting of a stem cell, a dental pulp cell, a periodontal ligament cell, a placenta, an amnion, and a fibroblast under a serum-free condition, further includes the step of: proliferating at least one type of cell selected from the group consisting of the stem cell, the dental pulp cell, the periodontal ligament cell, the placenta, the amnion, and the fibroblast in a serum-free culture medium containing at least three growth factors selected from the group consisting of FGF, PDGF, EGF, TGF-β, and HGF and at least one phospholipid before the step of differentiating at least one type of cell selected from the group consisting of the stem cell, the dental pulp cell, the periodontal ligament cell, the placenta, the amnion, and the fibroblast in the culture medium of the present invention.

A differentiation potential of a target cell can be kept high in a case where the target cell is cultured in a serum-free culture medium (hereinafter referred to as "serum-free proliferation culture medium") containing at least three growth factors selected from the group consisting of FGF, PDGF, EGF, TGF-β, and HGF and at least one phospholipids. It can be hypnotized that this is because (i) not all of the factors, which are contained in serum, for promoting growth of a target cell are contained in the serum-free proliferation culture medium, but no factor suppressing growth of the target cell are contained in the serum-free proliferation culture medium, and therefore (ii) growth potential and pluriopotency of the target cell can be kept higher as compared with a case where a serum-containing culture medium is used.

In a case where bone differentiation of a target cell that has been proliferation-cultured in the serum-free proliferation culture medium is induced in the culture medium of the present invention, the target cell whose growth potential and pluriopotency are kept high can be efficiently bone-differentiated in the culture medium of the present invention. This allows more efficient bone differentiation induction as compared with a case where bone differentiation of a target cell that has been cultured with the use of a general serum-containing proliferation culture medium is induced in the culture medium of the present invention. As a result, it is possible to further shorten a period of time required for the bone differentiation induction.

An osteoblast cell of the present invention is produced by the culture method of the present invention for inducing bone differentiation of at least one type of cell selected from the group consisting of a stem cell, a dental pulp cell, a periodontal ligament cell, a placenta, an amnion, and a fibroblast under a serum-free condition.

The osteoblast cell of the present invention shows higher alizarin red stainability, which indicates calcification of an osteoblast cell, as compared with an osteoblast cell differentiated by a conventional bone differentiation-inducing method using a conventional bone differentiation-inducing culture medium. That is, the osteoblast cell of the present invention is an osteoblast cell in which more calcium is deposited, as compared with an osteoblast cell differentiated by a conventional bone differentiation-inducing method using a conventional bone differentiation-inducing culture medium.

Accordingly, the osteoblast cell of the present invention cultured in a serum-free culture medium can be used for bone defect and osteoporosis in orthopedics, dentistry etc., and is therefore useful for regeneration medicine.

Advantageous Effects of Invention

As described above, a differentiation-inducing culture medium additive of the present invention for inducing bone differentiation of at least one type of cell selected from the group consisting of a stem cell, a dental pulp cell, a periodontal ligament cell, a placenta, an amnion, and a fibroblast under a serum-free condition, at least contains: at least one growth factor selected from the group consisting of EGF, FGF, and PDGF; dexamethasone; and β-glycerophosphate. Accordingly, by adding the differentiation-inducing culture medium additive of the present invention to a basal medium, it is possible to produce an effect that bone differentiation of a target cell can be efficiently induced under a serum-free condition and an effect that use of serum, which may include a pathogen and may cause variation in differentiation, can be avoided. Further, recombinant human insulin, transferrin, selenate, and ascorbic acid, which have been conventionally considered as being essential for bone differentiation induction, need not necessarily to be added. This makes it possible to provide a differentiation-inducing culture medium additive at lower cost.

BRIEF DESCRIPTION OF DRAWINGS

FIG. 3 shows a result of study on how EGF influenced induction of differentiation of mesenchymal stem cells into osteoblast cells in a case where a bone differentiation-inducing culture medium containing 10% FBS was used.

FIG. 4 shows a result of induction of differentiation of mesenchymal stem cells into osteoblast cells.

DESCRIPTION OF EMBODIMENTS

Figure 1:
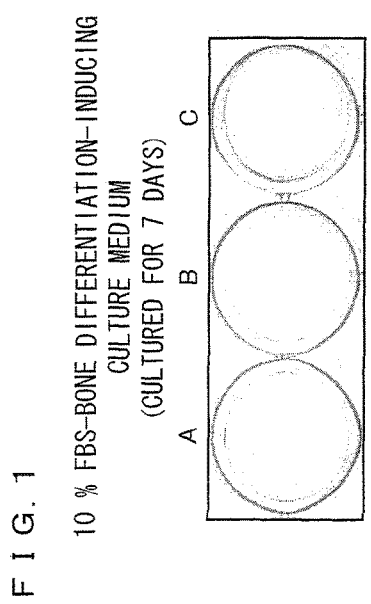
FIG. 1 shows an observation result of how differentiation of mesenchymal stem cells into osteoblast cells was induced in a case where a bone differentiation-inducing culture medium containing 10% FBS was used and in a case where a serum-free bone differentiation-inducing culture medium: B was used.
Figure 1:
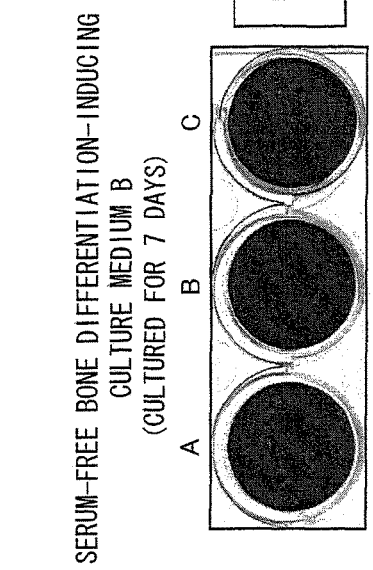
Figure 1:
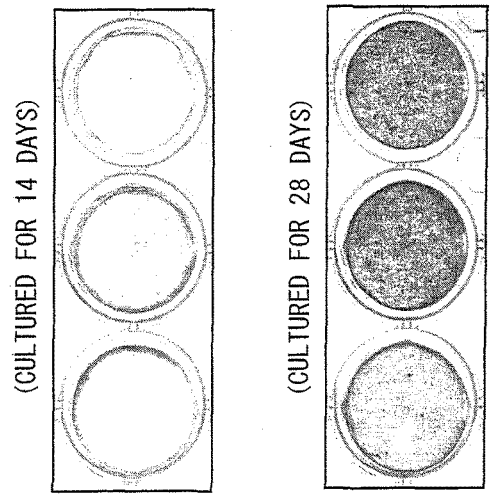
Figure 1:
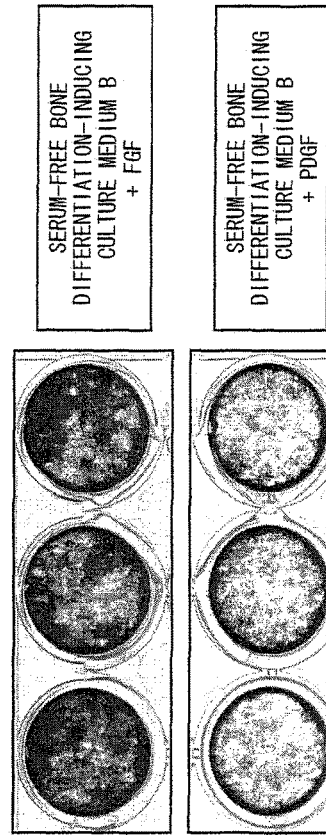
Figure 1:
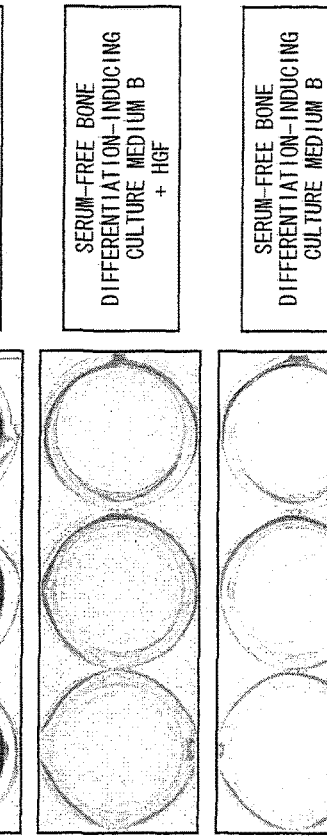

An embodiment of the present invention is described below. However, the present invention is not limited to this embodiment. Note that the phrase "A to B" indicative of a numerical range refers to "not less than A and not more than B" unless otherwise specified.

[1. Differentiation-inducing culture medium additive for inducing bone differentiation of at least one type of cell selected from the group consisting of a stem cell, a dental pulp cell, a periodontal ligament cell, a placenta, an amnion, and a fibroblast under a serum-free condition]

A differentiation-inducing culture medium additive of the present invention for inducing bone differentiation of at least one type of cell selected from the group consisting of a stem cell, a dental pulp cell, a periodontal ligament cell, a placenta, an amnion, and a fibroblast under a serum-free condition (hereinafter simply referred to as "differentiation-inducing culture medium additive of the present invention") at least contains at least one growth factor selected from the group consisting of EGF, FGF, and PDGF, dexamethasone, and β-glycerophosphate.

The "stem cell" used herein may be human-derived or animal-derived. The "stem cell" is not limited to a specific one, provided that it can differentiate into an osteoblast cell. Examples of the "stem cell" include an embryonic stem cell (an ES cell), an induced pluripotent stem cell (an iPS cell), and a somatic stem cell such as a mesenchymal stem cell.

The stem cell may be used in combination with a feeder cell or solely. The somatic stem cell may be a primary somatic stem cell taken from a tissue or an established somatic stem cell. Alternatively, the somatic stem cell may be a somatic stem cell obtained by differentiating the ES cell, iPS cell or the like. Further, the somatic stem cell may be, for example, a somatic stem cell that has not been differentiated completely or an undifferentiated somatic stem cell. Further, the stem cell to be differentiated may be a cell that has become confluent or a cell that has not become confluent yet.

For example, in a case where the mesenchymal stem cell is used as the stem cell, the stem cell can be, for example, bone marrow-derived, adipose-derived, periosteum-derived, synovium-derived, umbilical cord blood-derived, placenta-derived or finger-derived mesenchymal stem cell. Further, for example, in a case where the mesenchymal stem cell is differentiated into an osteoblast cell, the mesenchymal stem cell may be a mesenchymal stem cell that has not been differentiated into an osteoblast cell completely or an undifferentiated mesenchymal stem cell. Further, the mesenchymal stem cell to be differentiated may be a cell that has become confluent or a cell that has not become confluent yet.

Each of the dental pulp cell, periodontal ligament cell, placenta, amnion, and fibroblast may be human-derived or animal derived. Further, each of the dental pulp cell, periodontal ligament cell, placenta, amnion, and fibroblast may be used in combination with a feeder cell or solely. Further, each of the dental pulp cell, periodontal ligament cell, placenta, amnion, and fibroblast may be a primary cell taken from a tissue or an established cell.

The stem cell, dental pulp cell, periodontal ligament cell, placenta, amnion, and fibroblast may be used solely or in combination.

Dexamethasone and β-glycerophosphate are added to a basal medium in combination with the growth factor. This makes it possible to efficiently induce bone differentiation of a target cell under a serum-free condition. Specifically, it is possible to efficiently achieve formation of extracellular matrix and calcification of the osteoblast cell.

A used amount of these compounds is not limited in particular, but dexamethasone is preferably used in a range of $10^{-6}$ M to $10^{-10}$ M, more preferably in a range of $10^{-7}$ M to $10^{-9}$ M, which are final concentration in a culture medium to which the differentiation-inducing culture medium additive is added, and β-glycerophosphate is preferably used in a range of 1 mM to 100 mM, more preferably in a range of 1 mM to 30 mM, which are final concentration in a culture medium to which the differentiation-inducing culture medium additive is added.

The EGF is an abbreviation of an epidermal growth factor, and is intended to mean a growth factor selected from an EGF family. The EGF family includes, for example, EGF, TGF-α (transforming growth factor-α), amphiregulin, HB-EGF (heparin-binding EGF-like growth factor), epiregulin, and neuregulin. Since the EGF is most commonly used and most inexpensive in the EGF family, the EGF is preferable used.

The FGF is an abbreviation of a fibroblast growth factor, and is intended to mean a growth factor selected from an FGF family. The FGF is preferably FGF-2 (bFGF), but may be a different one, selected from the FGF family, such as FGF-1. The term "PDGF" used herein refers to a growth factor selected from a PDFG (platelet derived growth factor) family. The PDGF is preferably PFGF-BB or PDGF-AB.

It is only necessary that at least one growth factor selected from the group consisting of the EGF, FGF, and PDGF be contained in the differentiation-inducing culture medium additive of the present invention. Above all, the EGF or the PDGF is preferably used, and the EGF is especially preferably used, but it is also possible that two or more growth factors are used in any combination. Especially in a case where bone differentiation of a mesenchymal stem cell is induced, a combination of the EGF and FGF is preferably used, since use of the combination of the EGF and FGF makes it possible to induce differentiation of various different mesenchymal stem cell lines into an osteoblast cell and to promote the differentiation, as compared to a case where the EGF or FGF is used solely. Even in a case where other stem cells are used, two or more growth factors are preferably used in any combination since differentiation can be thus promoted.

An EGF content, a PDGF content, and an FGF content in the differentiation-inducing culture medium additive of the present invention are not limited in particular, but the EGF is preferably used in concentration of 0.5 ng/ml to 200 ng/ml, and the PDGF is preferably used in concentration of 0.5 ng/ml to 100 ng/ml, each of which concentration is final concentration in a culture medium to which the differentiation-inducing culture medium additive is added. The FGF is preferably used in concentration of 0.1 ng/ml to 10 µg/ml. For example, in a case where the bFGF is used as the FGF, the FGF is preferably used in concentration of 0.1 ng/ml to 100 ng/ml.

Note that each of the compounds and the growth factors may be a natural one or a synthetic one or may be produced by gene recombination etc., provided that it has activity as a growth factor.

The culture medium additive for use in serum-free culture of animal cells (Patent Literature 1) developed by the inventors of the present invention allows a stem cell to be proliferated at a speed equal to or faster than a case where a stem cell is cultured in a culture medium containing 10% serum while maintaining its properties (an osteogenic differentiation potential, an adipogenic differentiation potential etc. in the case of a mesenchymal stem cell). However, this culture medium additive cannot induce bone differentiation of a target cell (e.g., differentiation into an osteoblast cell, an adipose cell or the like in the case where the stem cell is a mesenchymal stem cell) under a serum-free condition. Accordingly, a conventional method requires the differentiation to be performed in the presence of serum.

In view of this, the inventors of the present invention studied a culture method which makes it possible to induce bone differentiation of a target cell even under a serum-free condition. As a result of the study, the inventors of the present invention found that it is possible to induce differentiation of a target cell into an osteoblast cell even under a serum-free condition by adding, to a basal mecium, a differentiation-inducing culture medium additive that at least contains at least one growth factor selected from the group consisting of EGF, FGF, and PDGF, dexamethasone, and β-glycerophosphate, and found that it is possible to efficiently induce especially differentiation of a mesenchymal stem cell into an osteoblast cell. Further, the inventors of the present invention found that use of a culture medium to which the differentiation-inducing culture medium additive of the present invention is added makes it possible to more efficiently induce bone differentiation and therefore makes it possible to shorten a period of time required for the bone differentiation induction, as compared with a case where bone differentiation induction is performed in the presence of serum.

In one embodiment, the differentiation-inducing culture medium additive of the present invention preferably further contains at least one phospholipid. Even in a case where a differentiation-inducing culture medium additive which contains no phospholipid is used, it is possible to induce bone differentiation of a target cell. However, in a case where at least one phospholipid is added to the differentiation-inducing culture medium additive, it is possible to further improve efficiency of bone differentiation induction of a target cell and to further shorten a period of time required for the bone differentiation induction. On this account, the differentiation-inducing culture medium additive of the present invention preferably further contains at least one phospholipid. Note that it was first discovered by the present invention that a phospholipid promotes bone differentiation induction of a target cell under a serum-free condition.

The phospholipid is not limited to a specific one. Examples of the phospholipid include phosphatidic acid, lysophosphatidic acid, phosphatidylinositol, phosphatidylserine, phosphatidylethanolamine, phosphatidyl choline, and phosphatidylglycerol. The differentiation-inducing culture medium additive of the present invention may contain these phospholipids solely or in combination. In a case where these phospholipids are used in combination, it is preferable that phosphatidic acid and phosphatidyl choline be used. Each of these phospholipids may be animal-derived or plant-derived.

A phospholipid content in the differentiation-inducing culture medium additive is not limited in particular, but it is preferable that one or more of the phospholipids be contained in the differentiation-inducing culture medium additive so that a culture medium to which the differentiation-inducing culture medium additive has been added contains the phospholipid alone or the phospholipids in total in a final concentration of 0.1 µg/ml to 30 µg/ml, most preferably in a final concentration of 10 µg/ml. Further, in a case where two or more of the phospholipids are used in combination, the phospholipids are preferably added so that the phospholipids are equal in final concentration to each other. In a case where the culture medium to which the differentiation-inducing culture medium additive is added contains the phospholipid alone or the phospholipids in total in a final concentration of more than 30 µg/ml, the phospholipid or the phospholipids may become toxic to the cell. Accordingly, such final concentration is not preferable.

The differentiation-inducing culture medium additive preferably contains an oxidation inhibitor. The oxidation inhibitor can prevent deterioration of the phospholipid. Examples of the oxidation inhibitor include DL-α-tocopherol acetate (vitamin E), dibutylhydroxytoluene (BHT), butylated hydroxyanisole (BHA), and catechin. DL-α-tocopherol acetate (vitamin E) is especially preferably used.

An oxidation inhibitor content in the differentiation-inducing culture medium additive is not limited in particular. However, the oxidation inhibitor is preferably used in concentration of 0.1 µg/ml to 50 µg/ml, which is final concentration in a culture medium to which the differentiation-inducing culture medium additive is added.

The differentiation-inducing culture medium additive may further contain insulin, transferrin, and selenate. Note, however, that the differentiation-inducing culture medium additive of the present invention does not necessarily need to contain insulin, transferrin, and selenate. Even in a case where the differentiation-inducing culture medium additive does not contain insulin, transferrin, and selenate, it is possible to sufficiently induce bone differentiation of a target cell. Since the differentiation-inducing culture medium additive of the present invention does not need to contain insulin, transferrin, and selenate that have been conventionally considered as being essential for bone differentiation induction of a stem cell, it is possible to induce bone differentiation at lower cost.

The insulin may be an insulin-like growth factor, and may be the one derived from a natural cell or the genetically modified one. An insulin content, a transferring content, and a selenate content in the differentiation-inducing culture medium additive are not limited in particular, but the insulin is preferably used in concentration of 0.5 µg/ml to 50 µg/ml, and the transferrin is preferably used in concentration of 0.5 µg/ml to 50 µg/ml, each of which concentration is final concentration in a culture medium to which the differentiation-inducing culture medium additive is added. The selenate is preferably used in concentration of 0.1 ng/ml to 50 ng/ml, more preferably in concentration of 0.5 ng/ml to 50 ng/ml.

The insulin, transferrin, and selenate may be commercially available ITS supplements. The insulin, transferrin, and selenate may be appropriately mixed or separately added to the differentiation-inducing culture medium additive.

The differentiation-inducing culture medium additive of the present invention may contain components other than the above-mentioned components as long as the effect of the present invention of inducing bone differentiation of a target cell under a serum-free condition is not ruined. For example, the differentiation-inducing culture medium additive of the present invention may contain other glucocorticoid such as cortisol, corticosterone, cortisone, and prednisolone. These components are preferably contained in concentration of $10^{-10}$ M to $10^{-6}$ M, more preferably in concentration of $10^{-9}$ M to $10^{-7}$ M, each of which concentration is final concentration in a culture medium to which the differentiation-inducing culture medium additive is added.

A method for preparing the differentiation-inducing culture medium additive of the present invention is not limited to a specific one, and can be a conventionally known method. For example, the differentiation-inducing culture medium additive of the present invention can be prepared by appropriately mixing the above-mentioned components (at least one growth factor selected from the group consisting of EGF, FGF, and PDGF, dexamethasone, β-glycerophosphate etc.).

An additive component such as excipient, binder, preservative, stabilizer, emulsifier, osmotic pressure controlling agent, or base agent may be added to the differentiation-inducing culture medium additive of the present invention according to need. The differentiation-inducing culture medium additive of the present invention can be formed into a medical preparation with the use of the additive component by a normal medical preparation formation method, and can be used as solid or liquid form such as tablet, power, granule, water-soluble powder, emulsion, oily agent, or suspension.

The differentiation-inducing culture medium additive is preferably used to induce differentiation of a mesenchymal stem cell into an osteoblast cell. The growth factor contained in the differentiation-inducing culture medium additive of the present invention has a function of promoting a bone differentiation program, and dexamethasone has a function of inducing a bone morphogenetic protein (BMP), and β-glycerophosphate has a function of supplying phosphoric acid and promoting calcification of an osteoblast cell. Accordingly, it is possible to efficiently induce bone differentiation of an osteoblast cell. In a case where the phospholipid is further added, it is possible to further promote the bone differentiation of the osteoblast cell. Accordingly, the differentiation-inducing culture medium additive of the present invention is also effective at promoting bone differentiation of an osteoblast cell.

[2. Culture medium for inducing differentiation of at least one type of cell selected from the group consisting of a stem cell, a dental pulp cell, a periodontal ligament cell, a placenta, an amnion, and a fibroblast under a serum-free condition]

A culture medium of the present invention for inducing bone differentiation of at least one type of cell selected from the group consisting of a dental pulp cell, a periodontal ligament cell, a placenta, an amnion, and a fibroblast under a serum-free condition (hereinafter simply referred to as "culture medium of the present invention") contains the components constituting the differentiation-inducing culture medium additive of the present invention and a basal medium, and contains no serum. The components refer to the components described in the Section[1.]. Specifically, the culture medium of the present invention at least contains at least one growth factor selected from the group consisting of EGF, FGF, and PDGF, dexamethasone, and β-glycerophosphate.

The culture medium of the present invention preferably further contains at least one phospholipid as one of the components since phospholipid can promote differentiation into an osteoblast cell under a serum-free condition.

Since it is only necessary that the culture medium contain the components constituting the differentiation-inducing culture medium additive of the present invention and a basal medium, the components may be added in the form of the differentiation-inducing culture medium additive described in the Section [1.] or the components described in the Section [1.] may be separately added to the basal medium.

The basal medium refers to a culture medium for animal cells, and can be a conventionally known culture medium for animal cells. Examples of the basal medium include a Ham's F12 medium, a α-MEM medium, a DMEM medium, an RPMI-1640 medium, and a MCDB201 medium. These basal media may be used solely or in combination. In one embodiment, the basal medium constituting the culture medium of the present invention is preferably a culture medium obtained by mixing the α-MEM medium and the MCDB201 medium at a ratio of 1:1.

The culture medium of the present invention can be obtained by mixing the components constituting the differentiation-inducing culture medium additive of the present invention and the basal medium. For example, the culture medium of the present invention can be prepared by adding, to the basal medium, the components described in the Section [1.] that have the final concentration described in the Section [1.]. The culture medium thus prepared is appropriately sterilized before use.

The culture medium allows differentiation of a target cell to be induced under a serum-free condition, but the culture medium is more preferably used to induce differentiation of a mesenchymal stem cell into an osteoblast cell. The culture medium of the present invention contains the components constituting the differentiation-inducing culture medium additive of the present invention. The growth factor contained in the differentiation-inducing culture medium additive has a function of promoting a bone differentiation program, and dexamethasone has a function of inducing a bone morphogenetic protein (BMP), and β-glycerophosphate has a function of supplying phosphoric acid and promoting calcification of an osteoblast cell. Accordingly, it is possible to efficiently induce bone differentiation of an osteoblast cell. In a case where the phospholipid is further added, it is possible to further promote the bone differentiation of the osteoblast cell. Accordingly, the culture medium of the present invention is also effective at promoting bone differentiation of an osteoblast cell.

[3. Culture method for inducing bone differentiation of at least one type of cell selected from the group consisting of a stem cell, a dental pulp cell, a periodontal ligament cell, a placenta, an amnion, and a fibroblast under a serum-free condition]

A culture method of the present invention for inducing bone differentiation of at least one type of cell selected from the group consisting of a stem cell, a dental pulp cell, a periodontal ligament cell, a placenta, an amnion, and a fibroblast under a serum-free condition (hereinafter simply referred to as "culture method of the present invention") includes the step of performing differentiation-culture of at least one type of cell selected from the group consisting of a stem cell, a dental pulp cell, a periodontal ligament cell, a placenta, an amnion, and a fibroblast in the culture medium of the present invention.

A culture condition is not limited in particular, provided that a target cell can be differentiated into an osteoblast cell. For example, in a case where a mesenchymal stem cell is used as the stem cell to be differentiated into an osteoblast cell, a mesenchymal stem cell that has been cultured in a DMEM medium containing 10% FBS so as to reach a confluent state is cultured in the culture medium of the present invention in the presence of 5% $CO_2$ at 37° C. for 7 or more days as described in the later-described Example. Thus, the mesenchymal stem cell can be differentiated into an osteoblast cell. However, the culture condition is not limited to this.

The culture method of the present invention for inducing bone differentiation of at least one type of cell selected from the group consisting of a stem cell, a dental pulp cell, a periodontal ligament cell, a placenta, an amnion, and a fibroblast under a serum-free condition preferably includes the step of performing proliferation-culture of at least one type of cell selected from the group consisting of a stem cell, a dental pulp cell, a periodontal ligament cell, a placenta, an amnion, and a fibroblast in a serum-free culture medium that contains at least three growth factors selected from the group consisting of FGF, PDGF, EGF, TGF-β, and HGF, and at least one phospholipid, before the step of performing differentiation-culture of at least one type of cell selected from the group consisting of a stem cell, a dental pulp cell, a periodontal ligament cell, a placenta, an amnion, and a fibroblast in the culture medium of the present invention.

In a case where bone differentiation induction of a target cell that has been cultured with the use of the serum-free proliferation culture medium is performed in the culture medium of the present invention, it is possible to more efficiently induce bone differentiation, as compared to a case where bone differentiation induction of a target cell that has been cultured with the use of a general serum-containing proliferation culture medium (e.g., DMEM medium containing 10% FBS) is performed in the culture medium of the present invention. As a result, it is possible to further shorten a period of time required for the bone differentiation induction.

The serum-free proliferation culture medium contains at least three growth factors selected from the group consisting of FGF, PDGF, EGF, TGF-β, and HGF, and at least one phospholipid, and contains no serum. The FGF, PDGF, EGF, and the phospholipid contained in the serum-free proliferation culture medium are as described in the Section [1.], and therefore are not explained repeatedly.

The TGF-β is an abbreviation of a transforming growth factor-β, and is intended to mean a growth factor selected from a TGF-β family. The TGF-β is preferably TGF-$β_3$, but may be a different one selected from the TGF-β family. The HGF is an abbreviation of a hepatocyte growth factor.

A growth factor content in the serum-free proliferation culture medium is not limited in particular, but the PDGF is preferably used in concentration of 0.5 ng/ml to 100 ng/ml, the TGF-β is preferably used in concentration of 0.5 ng/ml to 100 ng/ml, the EGF is preferably used in concentration of 0.5 ng/ml to 200 ng/ml, and the HGF is preferably used in concentration of 0.1 ng/ml to 50 ng/ml, each of which concentration is final concentration in the serum-free proliferation culture medium. The FGF is preferably used in concentration of 0.1 ng/ml to 10 μg/ml. For example, in a case where the bFGF is used as the FGF, the FGF is preferably used in concentration of 0.1 ng/ml to 100 ng/ml.

A phospholipid content in the differentiation-inducing culture medium additive is not limited in particular, but it is preferable that one or more of the phospholipids be contained in the differentiation-inducing culture medium additive so that a culture medium to which the differentiation-inducing culture medium additive has been added contains the phospholipid alone or the phospholipids in total in a final concentration of 0.1 μg/ml to 30 μg/ml, most preferably in a final concentration of 10 μg/ml. Further, in a case where two or more of the phospholipids are used in combination, the phospholipids are preferably added so that the phospholipids are equal in final concentration to each other. In a case where the culture medium to which the differentiation-inducing culture medium additive is added contains the phospholipid alone or the phospholipids in total in a final concentration of more than 30 μg/ml, the phospholipid or the phospholipids may become toxic to the cell. Accordingly, such final concentration is not preferable.

The serum-free proliferation culture medium may contain the phospholipids solely or in combination. In one embodiment, the serum-free proliferation culture medium contains a combination of phosphatidic acid and phosphatidyl choline.

The serum-free proliferation culture medium preferably further contains at least one fatty acid. Examples of the fatty acid contained in the serum-free proliferation culture medium include linoleic acid, linolenic acid, arachidonic acid, myristic acid, oleic acid, palmitoyl acid, palmitic acid, and stearic acid. The serum-free proliferation culture medium may contain these fatty acids solely or in combination. The serum-free proliferation culture medium may further contain cholesterol in addition to the above fatty acid. A fatty acid content in the serum-free proliferation culture medium is not limited in particular. However, in a case where a lipid concentrate (11905-031, produced by Gibco) is used, it is preferable that an undiluted solution of the lipid concentrate that is not less than $\frac{1}{1000}$ to not more than $\frac{1}{10}$ of the serum-free proliferation culture medium by volume is added.

The serum-free proliferation culture medium may further contain at least two factors selected from the group consisting of a connective tissue growth factor (CTGF), a vascular endothelial growth factor (VEGF), and an ascorbic acid compound.

The EGF and the ascorbic acid compound contained in the serum-free proliferation culture medium are as described in the Section [1.], and therefore are not explained repeatedly. The VEGF is intended to mean a growth factor selected from a VEGF family. The VEGF is preferably VEGF-A, but may be a different one, selected from the VEGF family, such as VEGF-B, VEGF-C, VEGF-D, VEGF-D, VEGF-E, P1GF (placental growth factor)-1 or P1GF-2.

A CTGF content, a VEGF content, and an ascorbic acid compound content in the serum-free proliferation culture medium are not limited in particular, but the CTGF is preferably used in concentration of 0.1 μg/ml to 20 μg/ml, the VEGF is preferably used in concentration of 0.5 ng/ml to 100 ng/ml, and the ascorbic acid compound is preferably used in concentration of 0.5 μg/ml to 200 μg/ml, each of which concentration is final concentration in the serum-free proliferation culture medium. For example, commercially available VEGF (v3388, produced by Sigma Aldrich, Inc.) and CTGF (036-19471, produced by Wako Pure Chemical Industries, Ltd.) can be used.

Further, the serum-free proliferation culture medium preferably contains a phospholipid oxidation inhibitor. The phospholipid oxidation inhibitor is as described in the Section [1.], and therefore is not explained repeatedly. In one embodiment, the serum-free proliferation culture medium contains DL-α-tocopherol acetate (vitamin E) as the phospholipid oxidation inhibitor. A phospholipid oxidation inhibitor content in the serum-free proliferation culture medium is not limited in particular, but the phospholipid oxidation inhibitor is preferably used in concentration of 0.1 μg/ml to 50 μg/ml, which is final concentration in the serum-free proliferation culture medium.

The serum-free proliferation culture medium may further contain a surfactant. In one embodiment, the serum-free proliferation culture medium contains Pluronic F-68 or Tween-80 as the surfactant.

The serum-free proliferation culture medium may further contain insulin, transferrin, and selenate. In addition, the serum-free proliferation culture medium may further contain dexamethasone or other glucocorticoid. The insulin, transferrin, selenate, dexamethasone, and other glucocorticoid are as described in the Section [1.], and therefore are not explained repeatedly. An insulin content, a transferrin content, and a selenate content in the serum-free proliferation culture medium are not limited in particular, but the insulin is preferably used in concentration of 0.5 μg/ml to 50 μg/ml, the transferrin is preferably used in concentration of 0.5 μg/ml to 50 μg/ml, and the selenate is preferably used in concentration of 0.1 ng/ml to 50 ng/ml, each of which concentration is final concentration in the serum-free proliferation culture medium. An amount of the otherglucocorticoid is not limited in particular, but the other glucocorticoid is preferably used in concentration of $10^{-10}$ M to $10^{-6}$ M, which is final concentration in the serum-free proliferation culture medium.

A method for preparing the serum-free proliferation culture medium is not limited to a specific one, and can be a conventionally known method. For example, the serum-free proliferation culture medium can be prepared by appropriately mixing, into a basal medium, the above-mentioned components (at least three growth factors selected from the group consisting of FGF, PDGF, EGF, TGF-β, and HGF and at least one phospholipid etc.). An exemplary embodiment of such a serum-free proliferation culture medium is serum-free STK2 medium used in the later-described Example.

A method for performing proliferation-culture of at least one type of cell selected from the group consisting of a stem cell, a dental pulp cell, a periodontal ligament cell, a placenta, an amnion, and a fibroblast with the use of the serum-free proliferation culture medium is not limited to a specific one, provided that a target cell is allowed to proliferate while preserving a differentiation potential of the target cell. For example, a mesenchymal stem cell seeded at a density of 5000 cells/cm$^2$ is cultured at 37° C. in the presence of 5% $CO_2$ while changing a culture medium every two or three days as described in the later-described Example. Thus, the mesenchymal stem cell is allowed to proliferate while preserving a differentiation potential of the mesenchymal stem cell. However, the method is not limited to this.

A degree of differentiation of a target cell into an osteoblast cell after culture can be examined with the use of a conventionally known bone differentiation marker. For example, a degree of differentiation of a target cell can be examined by staining the target cell with alizarin red.

The culture method allows bone differentiation of a target cell to be induced under a serum-free condition, but in particular, the culture method is more preferably used to induce differentiation of a mesenchymal stem cell into an osteoblast cell. The culture method of the present invention includes the step of culturing at least one type of cell selected from the group consisting of a stem cell, a dental pulp cell, a periodontal ligament cell, a placenta, an amnion, and a fibroblast in the culture medium of the present invention. The growth factor contained in the culture medium has a function of promoting a bone differentiation program, and dexamethasone has a function of inducing a bone morphogenetic protein (BMP), and β-glycerophosphate has a function of supplying phosphoric acid and promoting calcification of an osteoblast cell. Accordingly, it is possible to efficiently induce bone differentiation of an osteoblast cell. In a case where the phospholipid is further added, it is possible to further promote the bone differentiation of the osteoblast cell. Accordingly, the culture method of the present invention is also effective at promoting bone differentiation of an osteoblast cell.

[4. Kit for inducing differentiation of at least one type of cell selected from the group consisting of a stem cell, a dental pulp cell, a periodontal ligament cell, a placenta, an amnion, and a fibroblast under a serum-free condition]

A kit of the present invention for inducing bone differentiation of at least one type of cell selected from the group consisting of a stem cell, a dental pulp cell, a periodontal ligament cell, a placenta, an amnion, and a fibroblast under a serum-free condition (hereinafter simply referred to as "kit") includes the components constituting the differentiation-inducing culture medium additive of the present invention. The kit may further contain a basal medium.

That is, the kit contains at least one growth factor selected from the group consisting of EGF, FGF, and PDGF, dexamethasone, and β-glycerophosphate. The kit preferably further contains at least one phospholipid as one of the components since phospholipid can further promote differentiation.

The phospholipid is preferably selected from the group consisting of phosphatidic acid, lysophosphatidic acid, phosphatidylinositol, phosphatidylserine, phosphatidylethanolamine, phosphatidyl choline, and phosphatidylglycerol.

The kit may contain insulin, transferrin, and selenate.

The kit is not limited to the above arrangement, and can include other reagents and instruments. For example, the kit may include a culture plate for culturing a target cell and a reagent (e.g., alizarin red) for evaluating a degree of differentiation into an osteoblast cell or may include a target cell to be cultured.

The kit of the present invention may be provided as a single container that includes, in an appropriate amount and/or form, (i) differentiation-inducing culture medium additive, (ii) the compounds and the growth factors, or (iii) the compounds, the growth factors, the phospholipid, the basal medium, and other reagents. Alternatively, the kit of the present invention may be provided as a plurality of containers that include these components separately. Further, the kit of the present invention may include an instruction manual describing a procedure etc. for carrying out the method of the present invention.

Use of the kit of the present invention allows bone differentiation of a target cell to be induced under a serum-free condition, but in particular, the kit is more preferably used to induce differentiation of a mesenchymal stem cell into an osteoblast cell. The kit of the present invention includes the components constituting the differentiation-inducing culture medium additive of the present invention. The growth factor contained in the differentiation-inducing culture medium additive has a function of promoting a bone differentiation program, and dexamethasone has a function of inducing a bone morphogenetic protein (BMP), and β-glycerophosphate has a function of supplying phosphoric acid and promoting calcification of an osteoblast cell. Accordingly, it is possible to efficiently induce bone differentiation of an osteoblast cell. In a case where the phospholipid is further added, it is possible to further promote the bone differentiation of the osteoblast cell. Accordingly, the kit of the present invention is effective at promoting bone differentiation of an osteoblast cell.

[Osteoblast Cell]

An osteoblast cell of the present invention is produced by the culture method of the present invention for inducing bone differentiation of at least one type of cell selected from the group consisting of a stem cell, a dental pulp cell, a periodontal ligament cell, a placenta, an amnion, and a fibroblast under a serum-free condition. The culture method of the present invention for inducing bone differentiation of at least one type of cell selected from the group consisting of a stem cell, a dental pulp cell, a periodontal ligament cell, a placenta, an amnion, and a fibroblast under a serum-free condition is as described in the Section[3.], and therefore is not explained repeatedly.

The osteoblast cell of the present invention shows higher alizarin red stainability, which indicates calcification of an osteoblast cell, as compared with an osteoblast cell differentiated by a conventional bone differentiation-inducing method using a conventional bone differentiation-inducing culture medium, as described in the later-described Example. That is, the osteoblast cell of the present invention is an osteoblast cell in which more calcium is deposited, as compared with an osteoblast cell differentiated by a conventional bone differentiation-inducing method using a conventional bone differentiation-inducing culture medium.

Accordingly, the osteoblast cell of the present invention cultured in a serum-free culture medium can be used for bone defect and osteoporosis in orthopedics, dentistry etc., and is therefore useful for regeneration medicine.

The present invention is not limited to the description of the embodiments above, but may be altered by a skilled person within the scope of the claims. An embodiment based on a proper combination of technical means disclosed in different embodiments is encompassed in the technical scope of the present invention. Further, all of the academic documents and patent literatures described herein are incorporated herein by reference.

EXAMPLES

<Cell Culture Condition>

Mesenchymal stem cells were used as stem cells in Examples of the present invention. All the mesenchymal stem cells were cultured in a $CO_2$ incubator in the presence of 5% $CO_2$ at 37° C.

<STK2 Culture Medium>

A culture medium (a serum-free proliferation culture medium) used to proliferate and culture mesenchymal stem cells is referred to as an STK2 culture medium in the Examples of the present invention. The STK2 culture medium is a serum-free culture medium prepared by adding, to DMEM (produced by Sigma Aldrich, Inc.: D6046)/MCDB 201=1:1 as a basal medium, FGF-2, dexamethasone, a human insulin recombinant, transferrin, selenate, bovine serum albumin (BSA), a lipid concentrate (Chemically defined lipid concentrate), soybean lecithin, cholesterol, DL-α-tocopherol acetate, HGF, TGF-$\beta_3$, PDGF-BB, EGF, L-ascorbic acid 2-phosphate sesquimagnesium salt, phosphatidylcholine, phosphatidic acid salt, lithium chloride, reduced L-glutathione, Pluronic F-68, and Tween 80.

Table 1 shows a composition of the STK2 culture medium. The STK2 culture medium used in the Examples was prepared by adding components described in Table 1 to DMEM/MCDB 201=1:1 so that the components were used in respective final concentrations described in "Optimum Concentration" in Table 1.

TABLE 1

|  | Source | Effective concentration | Optimum concentration |
|---|---|---|---|
| Basal culture medium | | | |
| DMEM/MCDB201 | Sigma: D6046/M6770 | 1:1 | |
| Supplement A (Basal factor) | | | |
| (human recombinant) Basic fibroblast growth factor (bFGF) | Pepro Tech: 100-18B | 0.1-100 ng/ml | 3 ng/ml |
| Dexamethasone (Dex) | Sigma: D1756 | $10^{-6}$-$10^{-10}$ M | $10^{-8}$ M |
| (human recombinant) Insulin | Wako: 090-03446 | 0.5-50 μg/ml | 6.25 μg/ml |
| Transferrin | Sigma: T0665 | 0.5-50 μg/ml | 6.25 μg/ml |
| Selenous acid | Sigma: 21,117-6 | 0.1-50 ng/ml | 6.25 ng/ml |
| Bovine serum albumin (BSA) | Sigma: A8806 | 0.1-50 mg/ml | 1.25 mg/ml |
| Supplement B-1 (Basal lipid 1) | | | |
| Chemically defined lipid concentrate (CD) (Undiluted solution concentration: Arachidonic Acid 2.0 μg/ml, Cholesterol 220.00 μg/ml, DL-α-Tocopherol-Acetate 70.00 μg/ml, Linoleic Acid 540.00 μg/ml, Linolenic Acid 10.00 μg/ml, Myristic Acid 10.00 μg/ml, Oleic Acid 10.00 μg/ml, Palmitoleic Acid 10.0 μg/ml, Palmitic Acid 10.0 μg/ml, Stearic Acid 10.00 μg/ml, Pluronic F-68 100 mg/ml, Tween 80 2.2 mg/ml) | Gibco: 11905-031 | 1/1000-1/10 | 1/100 |
| Supplement B-2 (Basal lipid 2) | | | |
| Lecithin from Soybean (LS) | Wako: 120-00832 | 0.5-50 μg/ml | 10 μg/ml |
| cholesterol lipid concentrate (chol) | Gibco: 12531-018 | 0.1-30 μg/ml | 3 μg/ml |
| (+α)-Tocopherol-Acetate (VE) | Sigma: T1157 | 0.1-50 μg/ml | 2 μg/ml |
| Supplement C | | | |
| (human recombinant) Hepatocyte growth factor (HGF) | Sigma: H1404 | 0.1-50 ng/ml | 5 ng/ml |
| (human recombinant) Transforming growth factor-$\beta_3$ (TGF-$\beta_3$) | Pepro Tech: 100-36 | 0.5-100 ng/ml | 10 ng/ml |
| (human recombinant) Platelet derived growth factor (PDGF-BB) | Wako: 160-19741 | 0.5-100 ng/ml | 10 ng/ml |
| Others | | | |
| (human recombinant) Epidermal growth factor (EGF) | Wako: 050-07141 | 0.5-200 ng/ml | 20 ng/ml |
| Ascorbic acid 2-phosphate sesquimagnesium salt (VC) | Sigma: A8960 | 0.5-200 μg/ml | 50 μg/ml |
| Phosphatidylcholine (PC) | Wako: 163-21181 | (Total amount 0.1-30 μg/ml) | 5 μg/ml |
| Phosphatidic acid sodium salt (PA) | Sigma: P9511 | | 5 μg/ml |
| Lithium chloride | Sigma: L4408 | 0.1-5 mM | 1 mM |
| L-Glutahione (reduced) | Sigma: G6013 | 0.1-10 μg/ml | 2 μg/ml |

"Source" in Table 1 indicates from where substances described in Table 1 were obtained and their model numbers. "Effective concentration" indicates acceptable final concentrations in which the respective substances were contained in the STK2 culture medium. An effective concentration of the lipid concentrate (CD) is described as "1/1000 to 1/10". This means that an undiluted solution of lipid concentrate is added in a volume ratio of not less than 1/1000 and not more than 1/10 to the STK2 culture medium. Note that surfactants Pluronic F68 and Tween 80 are contained in the lipid concentrate.

Note also that "Optimum Concentration" in Table 1 indicates suitable amounts in which the respective substances were contained in the STK2 culture medium.

<STK0 Culture Medium>

A culture medium used to induce differentiation into osteoblast cells is referred to as an STK0 culture medium in the Examples of the present invention. The STK0 culture medium is a serum-free culture medium prepared by adding, to α-MEM (produced by Sigma Aldrich, Inc.: M4526)/MCDB 201=1:1 as a basal medium, FGF-2, dexamethasone, a human insulin recombinant, transferrin, selenate, bovine serum albumin (BSA), a lipid concentrate (Chemically defined lipid concentrate), soybean lecithin, cholesterol, DL-α-tocopherol acetate, HGF, TGF-$\beta_3$, PDGF-BB, EGF, L-ascorbic acid 2-phosphate sesquimagnesium salt, phosphatidylcholine, phosphatidic acid salt, lithium chloride, reduced L-glutathione, Pluronic F-68, and Tween 80.

Table 2 shows a composition of the STK0 culture medium. The STK0 culture medium used in the Examples was prepared by adding components described in Table 2 to α-MEM/MCDB 201=1:1 so that the components were used in respective final concentrations described in "Optimum Concentration" in Table 2.

TABLE 2

| | Source | Effective concentration | Optimum concentration |
|---|---|---|---|
| Basal culture medium | | | |
| α-MEM/MCDB201 | Sigma: M4526/M6770 | 1:1 | |
| Supplement A (Basal factor) | | | |
| Dexamethasone (Dex) | Sigma: D1756 | $10^{-6}$-$10^{-10}$ M | $10^{-8}$ M |
| Ascorbic acid 2-phosphate sesquimagnesium salt (VC) | Sigma: A8960 | 0.5-200 μg/ml | 50 μg/ml |
| (human recombinant) Insulin | Wako: 090-03446 | 0.5-50 μg/ml | 10 μg/ml |
| Transferrin | Sigma: T0665 | 0.5-50 μg/ml | 5.5 μg/ml |
| Selenous acid | Sigma: 211176 | 0.5-50 ng/ml | 6.7 ng/ml |
| Human serum albumin (HSA) | Sigma: A1887 | 0.1-50 mg/ml | 1.25 mg/ml |
| Supplement B-1 (Basal lipid) | | | |
| Chemically defined lipid concentrate (CD) (Undiluted solution concentration: Arachidonic Acid 2.0 μg/ml, Cholesterol 220.00 μg/ml, DL-α-Tocopherol-Acetate 70.00 μg/ml, Linoleic Acid 540.00 μg/ml, Linolenic Acid 10.00 μg/ml, Myristic Acid 10.00 μg/ml, Oleic Acid 10.00 μg/ml, Palmitoleic Acid 10.0 μg/ml, Palmitic Acid 10.0 μg/ml, Stearic Acid 10.00 μg/ml, Pluronic F-68 100 mg/ml, Tween 80 2.2 mg/ml) | Gibco: 11905-031 | 1/1000-1/10 | 1/100 |
| Supplement C (Phospholipid) | | | |
| Phosphatidylcholine (PC) | Wako: 163-21181 | (Total amount 0.1-30 μg/ml) | 5 μg/ml |
| Phosphatidic acid sodium salt (PA) | Sigma: P9511 | | 5 μg/ml |
| Supplement D (Growth factor) | | | |
| (human recombinant) Basic fibroblast growth factor (bFGF) | Kaken Pharmaceutical: KCB-1 | 0.01-20 ng/ml | 1 ng/ml |
| (human recombinant) Epidermal growth factor (EGF) | Wako: 050-07141 | 0.5-200 ng/ml | 20 ng/ml |
| (human recombinant) Platelet derived growth factor (PDGF-BB) | Wako: 160-19741 | 0.5-100 ng/ml | 10 ng/ml |
| (human recombinant) Hepatocyte growth factor (HGF) | Sigma: H1404 | 0.1-50 ng/ml | 5 ng/ml |
| (human recombinant) Transforming growth factor-$\beta_3$ (TGF-$\beta_3$) | Pepro Tech: 100-36 | 0.5-100 ng/ml | 10 ng/ml |
| Others | | | |
| Lithium chloride | Sigma: L4408 | 0.1-5 mM | 1 mM |
| L-Glutathione (reduced) | Sigma: G6013 | 0.1-10 μg/ml | 2 μg/ml |

"Source" in Table 2 indicates from where substances described in Table 2 were obtained and their model numbers. "Effective concentration" indicates acceptable final concentrations in which the respective substances were contained in the STK0 culture medium. An effective concentration of the lipid concentrate (CD) is described as "1/1000 to 1/10". This means that an undiluted solution of lipid concentrate is added in a volume ratio of not less than 1/1000 and not more than 1/10 to the STK0 culture medium. Note that surfactants Pluronic F68 and Tween 80 are contained in the lipid concentrate. "Optimum Concentration" indicates suitable amounts in which the respective substances were contained in the STK0 culture medium.

<Evaluation of Differentiation into Osteoblast Cells>

In the Examples of the present invention, evaluation of differentiation into osteoblast cells was carried out by staining differentiation-induced cells with alizarin red (produced by: Wako Pure Chemical Industries, Ltd., model number: 011-01192). The differentiation-induced cells were stained with alizarin red in accordance with a method described in an instruction manual of alizarin red.

Note that in the present description, a degree of differentiation into osteoblast cells was evaluated as "low", "moderate", and "high", judging from alizarin red stainability.

"Low" differentiation refers to differentiation at a stage where the differentiation-induced cells slightly stained with alizarin red can be visually observed. For example, a case where the differentiation-induced cells showed stainability as shown in a photograph of wells of "serum-free bone differentiation-inducing culture medium B+PDGF" in FIG. 1 was evaluated as "low" differentiation.

"Moderate" differentiation refers to differentiation at a stage where the differentiation-induced cells moderately stained with alizarin red can be visually observed. For example, a case where the differentiation-induced cells showed stainability as shown in a photograph of wells of "serum-free bone differentiation-inducing culture medium B+FGF" in FIG. 1 was evaluated as "moderate" differentiation.

"High" differentiation refers to differentiation at a stage where the differentiation-induced cells highly stained with alizarin red can be visually observed throughout a 24-well microplate. For example, a case where the differentiation-induced cells showed stainability as shown in a photograph of wells of "serum-free bone differentiation-inducing culture medium B+EGF" in FIG. 1 was evaluated as "high" differentiation.

Example 1

Study on Differentiation of Mesenchymal Stem Cells into Osteoblast Cells (1)

Three human ilium-marrow-derived mesenchymal stem cell lines (hereinafter referred to as a cell line A, a cell line B, and a cell line C) (purchased from Bio-Whittaker Inc. (Walkersville, Md.)) were used as mesenchymal stem cells. Note that the cell line A is a fifth subculture of human ilium-marrow-derived mesenchymal stem cells and each of the cell lines B and C is a fourth subculture of human ilium-marrow-derived mesenchymal stem cells. A DMEM culture medium containing 10% FBS was used to culture the mesenchymal stem cells. The mesenchymal stem cells were seeded on a 6-well microplate containing the DMEM culture medium at a density of 5000 cells/cm$^2$. Culture media were replaced every two or three days during the cell culture.

Note that the DMEM culture medium containing 10% FBS was prepared by adding fetal bovine serum (FBS) in a final concentration of 10% by weight to DMEM (produced by Sigma Aldrich, Inc.: D-6046)/MCDB 201 (produced by Sigma Aldrich, Inc.: M-6670)=1:1 as a basal medium.

The mesenchymal stem cells were washed two times with PBS before becoming confluent. Then, the mesenchymal stem cells were incubated for two minutes in PBS containing 0.05% trypsin and 0.2 mM EDTA, so that the mesenchymal stem cells were detached from the microplate. Then, the mesenchymal stem cells were re-suspended with a plant-derived trypsin inhibitor (Produced by Sigma Aldrich, Inc.: T6522) that contained no serum.

Subsequently, the mesenchymal stem cells were washed three times with a serum-free DMEM culture medium. Then, the mesenchymal stem cells were seeded on a 24-well microplate at a density of 10000 cells/cm$^2$ in such a manner that the mesenchymal stem cells per cell line were seeded on two (n=2) wells for each condition. The mesenchymal stem cells were cultured in the serum-free STK2 culture medium at 37° C. in a $CO_2$ incubator with 5% $CO_2$ until becoming confluent.

The 24-well microplate to which bottom surface the mesenchymal stem cells were attached was washed two times with the serum-free DMEM culture medium on the fourth day of the culture. Then, the mesenchymal stem cells were cultured in respective culture media shown in Table 3 for 3 days, 7 days, 14 days, or 21 days. An old culture medium was replaced with an identical new one every two or three days during differentiation induction. On the third or seventh day of the culture for differentiation in the respective culture media shown in Table 3, evaluation of differentiation into osteoblast cells was carried out by staining the mesenchymal stem cells with alizarin red.

Bone differentiation-inducing culture media shown in Table 3 and used in Example 1 are described here. "10% FBS-DMEM" is the DMEM culture medium containing 10% FBS in Table 3. The "10% FBS-DMEM" was used as a control culture medium. Note that "10% FBS-bone differentiation-inducing culture medium" was prepared by adding, to α-MEM, FBS in a final concentration of 10% by weight, dexamethasone in a final concentration of 100 nM, β-glycerophosphate in a final concentration of 10 mM, and L-ascorbic acid 2-phosphate sesquimagnesium salt in a final concentration of 50 μg/ml. The "10% FBS-bone differentiation-inducing culture medium" is identical to a conventionally publicly-known bone differentiation-inducing culture medium used in Patent Literature 1.

"Serum-free bone differentiation-inducing culture medium: A" was prepared by adding, to the STK0 culture medium which is a serum-free culture medium, β-glycerophosphate in a final concentration of 10 mM. "A–(FGF-2)" was prepared by removing FGF-2 from the serum-free bone differentiation-inducing culture medium: A. Note that in the present description, the removal of FGF-2 from the serum-free bone differentiation-inducing culture medium: A can be carried out by, for example, preparing the serum-free bone differentiation-inducing culture medium: A to which only FGF-2 is not added. Same hereinafter applies to "TGF-$β_3$ was removed from the serum-free bone differentiation-inducing culture medium: A" etc. "A–(TGF-$β_3$)" was prepared by removing TGF-$β_3$ from the serum-free bone differentiation-inducing culture medium: A. "A–HGF" was prepared by removing HGF from the serum-free bone differentiation-inducing culture medium: A. "A–EGF" was prepared by removing EGF from the serum-free bone differentiation-inducing culture medium: A. "A–(PDGF-BB)" was prepared by removing PDGF-BB from the serum-free bone differentiation-inducing culture medium: A.

"Serum-free bone differentiation-inducing culture medium: B" was prepared by removing FGF-2, TGF-$β_3$, HGF, EGF, and PDGF-BB from the serum-free bone differentiation-inducing culture medium: A. "B+EGF" was prepared by adding EGF in a final concentration of 20 ng/ml to the serum-free bone differentiation-inducing culture medium: B. "B+(FGF-2)" was prepared by adding FGF-2 in a final concentration of 1 ng/ml to the serum-free bone differentiation-inducing culture medium: B. "B+(TGF-$β_3$)" was prepared by adding TGF-$β_3$ in a final concentration of 10 ng/ml to the serum-free bone differentiation-inducing culture medium: B. "B+HGF" was prepared by adding HGF in a final concentration of 5 ng/ml to the serum-free bone differentiation-inducing culture medium: B. "B+(PDGF- BB)" was prepared by adding PDGF-BB in a final concentration of 10 ng/ml to the serum-free bone differentiation-inducing culture medium: B.

Figure 2:
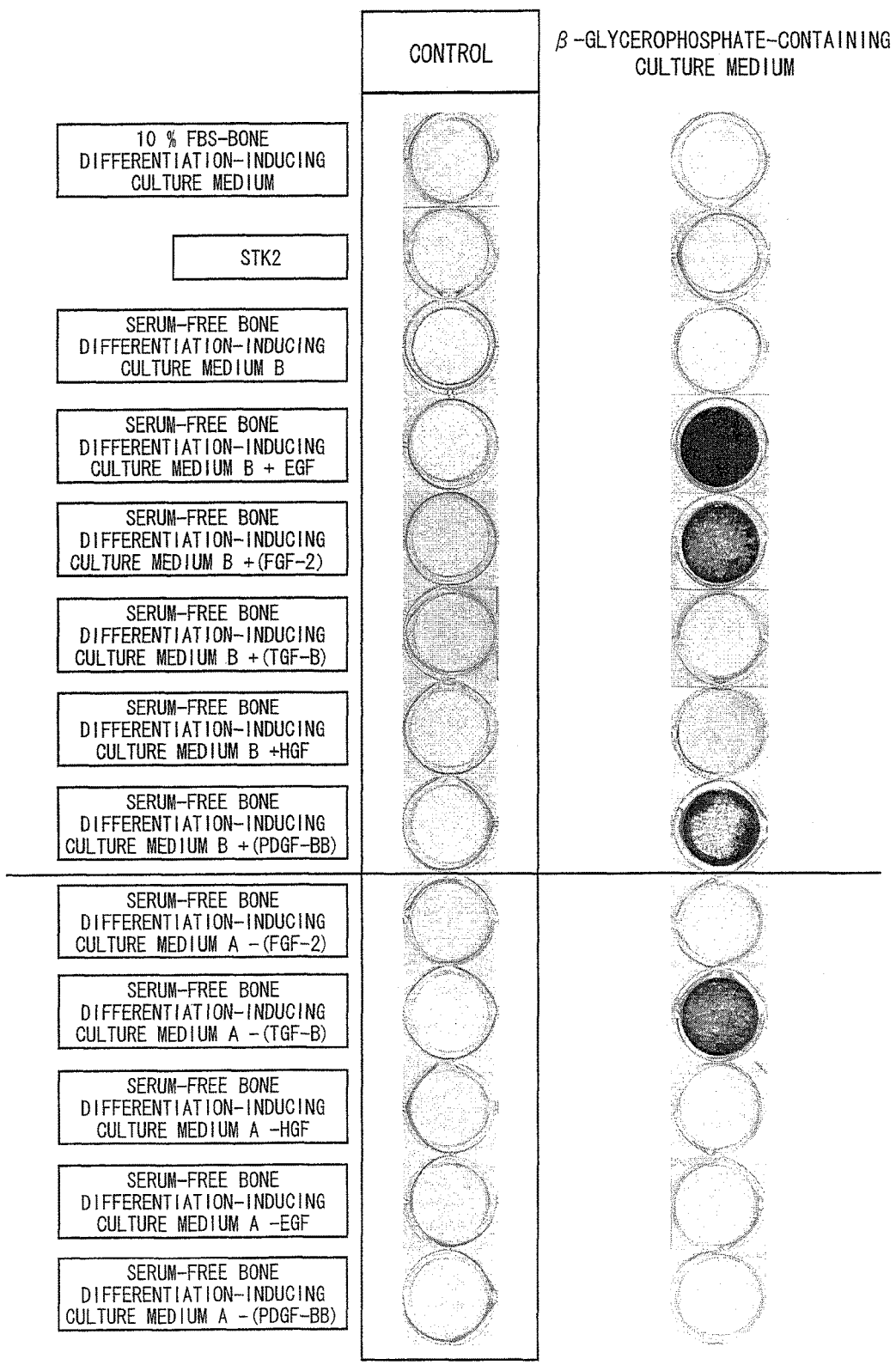
FIG. 2 shows a result of study on how a growth factor influenced induction of differentiation of mesenchymal stem cells into osteoblast cells.

Table 3 and FIGS. 1 through 3 show results. FIG. 1 shows an observation result of how differentiation of mesenchymal stem cells into osteoblast cells was induced in a case where the "10% FBS-bone differentiation-inducing culture medium", i.e., a conventionally publicly-known bone differentiation-inducing culture medium containing 10% FBS was used and a case where the serum-free bone differentiation-inducing culture medium: B was used. The observation result was obtained for three samples per culture medium. The three samples are the cell lines A, B, and C from the left. FIG. 2 shows a result of study on how a growth factor influenced induction of differentiation of mesenchymal stem cells into osteoblast cells. FIG. 3 shows a result of study on how EGF influenced induction of differentiation of mesenchymal stem cells into osteoblast cells in a case where a bone differentiation-inducing culture medium containing 10% FBS was used.

In a case where the culture medium prepared by adding EGF to the serum-free bone differentiation-inducing culture medium: B was used, moderate differentiation was observed on the third day of the culture, and differentiation induction was much more advanced on the seventh day of the culture than on the twenty-first day of the culture carried out by use of the bone differentiation-inducing culture medium containing 10% FBS (see FIG. 1 and Table 3). As described earlier, the serum-free bone differentiation-inducing culture medium: B was prepared by removing EGF, TGF-$\beta_3$, HGF, FGF-2, and PDGF-BB from the culture medium prepared by adding 10 mM of β-glycerophosphate to the STK0 culture medium. Namely, the serum-free bone differentiation-inducing culture medium: B was prepared by causing a basal medium (in which MCDB and α-MEM were mixed in a ratio of 1:1) to contain dexamethasone, L-ascorbic acid 2-phosphate sesquimagnesium salt, β-glycerophosphate, fatty acids (linoleic acid, linolenic acid, arachidonic acid,

TABLE 3

| Culture medium type | Result of bone differentiation | |
|---|---|---|
| | 3rd day | 7th day |
| 1. 10% FBS-DMEM | Undifferentiated | Undifferentiated |
| 2. 10% FBS-bone differentiation-inducing culture medium | Undifferentiated | Undifferentiated |
| 3. Serum-free bone differentiation-inducing culture medium: A (STK0 + 10 mM β-glycerophosphate) | Undifferentiated | Undifferentiated |
| 4. A - (FGF-2) | Undifferentiated | Undifferentiated |
| 5. A - (TGF-$\beta_3$) | Differentiated (Low) | Differentiated (Moderately) |
| 6. A - HGF | Undifferentiated | Undifferentiated |
| 7. A - EGF | Undifferentiated | Undifferentiated |
| 8. A - (PDGF-BB) | Undifferentiated | Undifferentiated |
| 9. Serum-free bone differentiation-inducing culture medium: B (A - EGF - (TGF-$\beta_3$) - HGF - (FGF-2) - (PDGF-BB)) | Undifferentiated | Undifferentiated |
| 10. B + EGF | Differentiated (Moderately) | Differentiated (Highly) |
| 11. B + (FGF-2) | Undifferentiated | Differentiated (Moderately) |
| 12. B + (TGF-$\beta_3$) | Undifferentiated | Undifferentiated |
| 13. B + HGF | Undifferentiated | Undifferentiated |
| 14. B + (PDGF-BB) | Undifferentiated | Differentiated (Low) |

In a case where the DMEM culture medium containing 10% FBS was used, no differentiation into osteoblast cells was observed even on the seventh day of the culture (see Table 3). In a case where the bone differentiation-inducing culture medium containing 10% FBS was used, the mesenchymal stem cells were in an undifferentiated state on the seventh day of the culture. However, on the fourteenth day of the culture, the mesenchymal stem cells showed alizarin red stainability, which indicates calcification of an osteoblast cell, and deposition of calcium was observed as shown in FIG. 1. Further, deposition of calcium was noticeable on the twenty-first day of the culture.

The serum-free bone differentiation-inducing culture medium: B shown in FIG. 1 refers to the serum-free bone differentiation-inducing culture medium: B shown in Table 3. The serum-free bone differentiation-inducing culture medium: B was prepared by removing EGF, TGF-$\beta_3$, HGF, FGF-2, and PDGF-BB from a culture medium prepared by adding 10 mM of β-glycerophosphate to the STK0 culture medium. For example, "serum-free bone differentiation-inducing culture medium: B+EGF" in FIG. 1 was prepared by adding EGF in a final concentration of 20 ng/ml to the serum-free bone differentiation-inducing culture medium: B. Same applies to "serum-free bone differentiation-inducing culture medium: B+FGF" etc.

myristic acid, oleic acid, palmitoyl acid, palmitic acid, and stearic acid), and phospholipids (phosphatidic acid and phosphatidylcholine), cholesterol, an oxidation inhibitor DL-α-tocopherol acetate (vitamin E), surfactants Pluronic F-68 and Tween 80, etc. This revealed that addition of EGF to the serum-free bone differentiation-inducing culture medium: B highly promoted induction of differentiation into osteoblast cells in a much shorter period as compared to the case where the bone differentiation-inducing culture medium containing 10% FBS was used.

In a case where the culture medium prepared by adding FGF-2 to the serum-free bone differentiation-inducing culture medium: B was used, the mesenchymal stem cells were in the undifferentiated state on the third day of the culture. On the seventh day of the culture, moderate differentiation into osteoblast cells was observed and differentiation induction was much more advanced than on the twenty-first day of the culture carried out by use of the bone differentiation-inducing culture medium containing 10% FBS (see FIG. 1 and Table 3). Further, in a case where the culture medium prepared by adding PDGF-BB to the serum-free bone differentiation-inducing culture medium: B was used, the mesenchymal stem cells were in the undifferentiated state on the third day of the culture. However, on the seventh day of the culture, low differentiation was observed and was more noticeable than on the fourteenth day of the culture carried out by use of the bone differentiation-inducing culture medium containing 10% FBS.

In FIG. 2, for example, "serum-free bone differentiation-inducing culture medium: B+EGF" refers to a culture medium prepared by adding EGF in a final concentration of 20 ng/ml to the serum-free bone differentiation-inducing culture medium: B. In FIG. 2, for example, "serum-free bone differentiation-inducing culture medium: A−(FGF-2)" refers to a culture medium prepared by removing FGF-2 from the serum-free bone differentiation-inducing culture medium: A. A culture period in FIG. 2 is set to seven days. Among the cases where the serum-free bone differentiation-inducing culture medium: A was used, only in a case where the serum-free bone differentiation-inducing culture medium: A from which TGF-$\beta_3$ was removed was used, differentiation was observed (see FIG. 2 and Table 3). In contrast, no differentiation was observed in a case where the serum-free bone differentiation-inducing culture medium: B to which TGF-$\beta_3$ was added was used. This revealed that some growth factors such as EGF, FGF-2, and PDGF-BB are suitable and other growth factors such as TGF-$\beta_3$ are unsuitable to cause mesenchymal stem cells to differentiate into osteoblast cells.

Note that in FIG. 2, a photograph of wells in a left column indicated as "control" shows an experimental plot in which no β-glycerophosphate is contained and a photograph of wells in a right column shows an experimental plot in which β-glycerophosphate is contained in a final concentration of 10 mM.

FIG. 3 shows that addition of EGF to the 10% FBS-bone differentiation-inducing culture medium promotes differentiation into osteoblast cells. However, differentiation in an experimental plot (see FIG. 3) in which EGF was added to the 10% FBS-bone differentiation-inducing culture medium was less advanced even on the fourteenth day of the culture than that in an experimental plot (see FIG. 1) in which EGF was added to the serum-free bone differentiation-inducing culture medium: B.

Example 2

Study on Differentiation of Mesenchymal Stem Cells into Osteoblast Cells (2)

Five human ilium-marrow-derived mesenchymal stem cell lines (hereinafter referred to as a cell line F, a cell line G, a cell line H, a cell line I, and a cell line J) (purchased from Bio-Whittaker Inc. (Walkersville, Md.)) were used as mesenchymal stem cells. Note that each of the cell lines F, H, and I is a fifth subculture of human ilium-marrow-derived mesenchymal stem cells and each of the cell lines G and J is a fourth subculture of human ilium-marrow-derived mesenchymal stem cells. A DMEM culture medium containing 10% FBS was used to proliferate and culture the mesenchymal stem cells. The mesenchymal stem cells were seeded on a 6-well microplate containing the DMEM culture medium containing 10% FBS at a density of 5000 cells/cm². Culture media were replaced every two or three days during the cell culture.

Before becoming confluent, the mesenchymal stem cells were collected from the 6-well microplate by a method similar to that of Example 1. Subsequently, the mesenchymal stem cells were washed three times with the DMEM culture medium containing 10% FBS. Then, the mesenchymal stem cells were seeded on a 24-well microplate at a density of 10000 cells/cm² in such a manner that the mesenchymal stem cells per cell line were seeded on two (n=2) wells for each condition. The mesenchymal stem cells were cultured in the DMEM culture medium containing 10% FBS until becoming confluent.

The 24-well microplate to which the mesenchymal stem cells were attached was washed two times with a serum-free DMEM culture medium on the fourth day of the culture. Then, the mesenchymal stem cells were cultured in respective culture media shown in Table 4 for 7 days, 14 days, or 21 days. An old culture medium was replaced with an identical new one every two or three days during differentiation induction. On the seventh, fourteenth, or twenty-first day of the culture for differentiation in the respective culture media shown in Table 4, evaluation of differentiation of the mesenchymal stem cells into osteoblast cells was carried out by staining the mesenchymal stem cells with alizarin red.

Bone differentiation-inducing culture media shown in Table 4 and used in Example 2 are described here. "10% FBS-bone differentiation-inducing culture medium" in FIG. 4 is identical to that used in Example 1. Further, "10% FBS-bone differentiation-inducing culture medium (α:M=1:1)" is identical to "10% FBS-bone differentiation-inducing culture medium" used in Example 1 except that "10% FBS-bone differentiation-inducing culture medium (α:M=1:1)" was prepared by replacing the basal medium α-MEM of the "10% FBS-bone differentiation-inducing culture medium" used in Example 1 with a basal medium in which α-MEM and MCDB201 were mixed in a ratio of 1:1.

"Serum-free bone differentiation-inducing culture medium: B" is identical to that used in Example 1. "B+EGF", "B+(FGF-2)", "B+(TGF-$\beta_3$)", "B+HGF", and "B+(PDGF-BB)" culture media are also identical to those used in Example 1.

"Serum-free bone differentiation-inducing culture medium: C" was prepared by adding FGF-2 and EGF in respective final concentrations of 1 ng/ml and 20 ng/ml to the serum-free bone differentiation-inducing culture medium: B. "C−Dex" was prepared by removing dexamethasone from the serum-free bone differentiation-inducing culture medium: C. "C−VC" was prepared by removing L-ascorbic acid 2-phosphate sesquimagnesium salt from the serum-free bone differentiation-inducing culture medium: C. "C−(β-glycerophosphate)" was prepared by removing β-glycerophosphate from the serum-free bone differentiation-inducing culture medium: C. "C−PA−PC" was prepared by removing phosphatidylcholine and phosphatidic acid salt from the serum-free bone differentiation-inducing culture medium: C. "C−CD" was prepared by removing a lipid concentrate from the serum-free bone differentiation-inducing culture medium: C. "C−LiCl" was prepared by removing LiCl from the serum-free bone differentiation-inducing culture medium: C. "C−ITS" was prepared by removing insulin, transferrin, and selenate from the serum-free bone differentiation-inducing culture medium: C. "C−CD−LiCl" was prepared by removing the lipid concentrate and LiCl from the serum-free bone differentiation-inducing culture medium: C. "C−CD−LiCl−VC+(PDGF-BB)" was prepared by adding PDGF-BB in a final concentration of 10 ng/ml to a culture medium obtained by removing, from the serum-free bone differentiation-inducing culture medium: C, the lipid concentrate, LiCl, and L-ascorbic acid 2-phosphate sesquimagnesium salt. Table 4 shows a result of bone differentiation which result was obtained on the seventh day after the beginning of differentiation induction. Table 5 shows a result of bone differentiation which result was obtained on the fourteenth day after the beginning of differentiation induction. Table 6 shows a result of bone differentiation which result was obtained on the twenty-first day after the beginning of differentiation induction.

TABLE 4

| Culture medium type | Result of bone differentiation 7th day | | | | |
|---|---|---|---|---|---|
| | cell line F | cell line G | cell line H | cell line I | cell line J |
| 1. 10% FBS-bone differentiation-inducing culture medium | Undifferentiated | Undifferentiated | Undifferentiated | Undifferentiated | Undifferentiated |
| 2. 10% FBS-bone differentiation-inducing culture medium (α:M = 1:1) | Undifferentiated | Undifferentiated | Undifferentiated | Undifferentiated | Undifferentiated |
| 3. Serum-free bone differentiation-inducing culture medium: B | Undifferentiated | Undifferentiated | Undifferentiated | Undifferentiated | Undifferentiated |
| 4. B + (FGF-2) | Undifferentiated | Undifferentiated | Undifferentiated | Undifferentiated | Undifferentiated |
| 5. B + EGF | Differentiated (Low) | Differentiated (Moderately) | Undifferentiated | Undifferentiated | Undifferentiated |
| 6. B + (TGF-β$_3$) | Undifferentiated | Undifferentiated | Undifferentiated | Undifferentiated | Undifferentiated |
| 7. B + HGF | Undifferentiated | Undifferentiated | Undifferentiated | Undifferentiated | Undifferentiated |
| 8. B + (PDGF-BB) | Differentiated (Low) | Differentiated (Low) | Undifferentiated | Differentiated (Low) | Differentiated (Low) |
| 9. Serum-free bone differentiation-inducing culture medium: C (Serum-free bone differentiation-inducing culture medium: B + FGF + EGF) | Differentiated (Low) | Differentiated (Low) | Differentiated (Low) | Undifferentiated | Undifferentiated |
| 10. C - Dex | Undifferentiated | Undifferentiated | Undifferentiated | Undifferentiated | Undifferentiated |
| 11. C - VC | Differentiated (Low) | Differentiated (Moderately) | Differentiated (Low) | Undifferentiated | Undifferentiated |
| 12. C - β-glycerophosphate) | Undifferentiated | Undifferentiated | Undifferentiated | Undifferentiated | Undifferentiated |
| 13. C - PA - PC | Undifferentiated | Undifferentiated | Undifferentiated | Undifferentiated | Undifferentiated |
| 14. C - CD | Differentiated (Highly) | Differentiated (Highly) | Differentiated (Low) | Differentiated (Low) | Differentiated (Moderately) |
| 15. C - LiCl | Differentiated (Low) | Differentiated (Moderately) | Differentiated (Low) | Undifferentiated | Differentiated (Low) |
| 16. C - ITS | Differentiated (Low) | Undifferentiated | Undifferentiated | Undifferentiated | Undifferentiated |
| 17. C - CD - LiCl | Undifferentiated | Differentiated (Highly) | Differentiated (Low) | Undifferentiated | Differentiated (Low) |
| 18. C - CD - LiCl - VC + (PDGF-BB) | Differentiated (Highly) | Differentiated (Moderately) | Differentiated (Low) | Differentiated (Low) | Differentiated (Moderately) |

TABLE 5

| Culture medium type | Result of bone differentiation 14th day | | | | |
|---|---|---|---|---|---|
| | cell line F | cell line G | cell line H | cell line I | cell line J |
| 1. 10% FBS-bone differentiation-inducing culture medium | Undifferentiated | Differentiated (Low) | Undifferentiated | Differentiated (Low) | Differentiated (Low) |
| 2. 10% FBS-bone differentiation-inducing culture medium (α:M = 1:1) | Undifferentiated | Undifferentiated | Differentiated (Low) | Differentiated (Low) | Differentiated (Low) |
| 3. Serum-free bone differentiation-inducing culture medium: B | Undifferentiated | Undifferentiated | Undifferentiated | Undifferentiated | Undifferentiated |
| 4. B + (FGF-2) | Undifferentiated | Differentiated (Low) | Undifferentiated | Undifferentiated | Undifferentiated |
| 5. B + EGF | Differentiated (Highly) | Differentiated (Highly) | Differentiated (Moderately) | Undifferentiated | Differentiated (Moderately) |
| 6. B + (TGF-β$_3$) | Undifferentiated | Differentiated (Low) | Undifferentiated | Undifferentiated | Undifferentiated |
| 7. B + HGF | Undifferentiated | Undifferentiated | Undifferentiated | Undifferentiated | Undifferentiated |
| 8. B + (PDGF-BB) | Differentiated (Moderately) | Differentiated (Moderately) | Differentiated (Moderately) | Differentiated (Moderately) | Differentiated (Moderately) |
| 9. Serum-free bone differentiation-inducing culture medium: C (Serum-free bone differentiation-inducing culture medium: B + FGF + EGF) | Differentiated (Highly) | Differentiated (Moderately) | Differentiated (Highly) | Undifferentiated | Differentiated (Moderately) |
| 10. C - Dex | Undifferentiated | Undifferentiated | Undifferentiated | Undifferentiated | Undifferentiated |
| 11. C - VC | Differentiated (Highly) | Differentiated (Highly) | Differentiated (Low) | Undifferentiated | Differentiated (Moderately) |
| 12. C - β-glycerophosphate) | Undifferentiated | Undifferentiated | Undifferentiated | Undifferentiated | Undifferentiated |
| 13. C - PA - PC | Undifferentiated | Differentiated (Low) | Undifferentiated | Undifferentiated | Undifferentiated |
| 14. C - CD | Differentiated (Highly) | Differentiated (Highly) | Differentiated (Moderately) | Differentiated (Moderately) | Differentiated (Highly) |
| 15. C - LiCl | Differentiated (Moderately) | Differentiated (Highly) | Differentiated (Moderately) | Undifferentiated | Differentiated (Highly) |
| 16. C - ITS | Differentiated (Low) | Differentiated (Highly) | Undifferentiated | Undifferentiated | Undifferentiated |

TABLE 5-continued

| | Result of bone differentiation 14th day | | | | |
|---|---|---|---|---|---|
| Culture medium type | cell line F | cell line G | cell line H | cell line I | cell line J |
| 17. C − CD − LiCl | Differentiated (Moderately) | Differentiated (Highly) | Differentiated (Moderately) | Differentiated (Moderately) | Differentiated (Highly) |
| 18. C − CD − LiCl − VC + (PDGF-BB) | Differentiated (Highly) | Differentiated (Highly) | Differentiated (Moderately) | Differentiated (Highly) | Differentiated (Highly) |

TABLE 6

| | Result of bone differentiation 21st day | | | | |
|---|---|---|---|---|---|
| Culture medium type | cell line F | cell line G | cell line H | cell line I | cell line J |
| 1. 10% FBS-bone differentiation-inducing culture medium | Differentiated (Low) | Differentiated (Low) | Differentiated (Low) | Differentiated (Moderately) | Differentiated (Low) |
| 2. 10% FBS-bone differentiation-inducing culture medium (α:M = 1:1) | Differentiated (Low) | Undifferentiated | Differentiated (Low) | Differentiated (Low) | Differentiated (Moderately) |
| 3. Serum-free bone differentiation-inducing culture medium: B | Undifferentiated | Undifferentiated | Undifferentiated | Undifferentiated | Undifferentiated |
| 4. B + (FGF-2) | Undifferentiated | Differentiated (Moderately) | Undifferentiated | Undifferentiated | Undifferentiated |
| 5. B + EGF | Differentiated (Highly) | Differentiated (Highly) | Differentiated (Highly) | Undifferentiated | Differentiated (Moderately) |
| 6. B + (TGF-$\beta_3$) | Undifferentiated | Differentiated (Low) | Undifferentiated | Undifferentiated | Undifferentiated |
| 7. B + HGF | Undifferentiated | Undifferentiated | Undifferentiated | Undifferentiated | Undifferentiated |
| 8. B + (PDGF-BB) | Differentiated (Highly) | Differentiated (Highly) | Differentiated (Highly) | Differentiated (Highly) | Differentiated (Moderately) |
| 9. Serum-free bone differentiation-inducing culture medium: C (Serum-free bone differentiation-inducing culture medium: B + FGF + EGF) | Differentiated (Highly) | Differentiated (Highly) | Differentiated (Highly) | Undifferentiated | Differentiated (Moderately) |
| 10. C − Dex | Undifferentiated | Undifferentiated | Undifferentiated | Undifferentiated | Undifferentiated |
| 11. C − VC | Differentiated (Highly) | Differentiated (Highly) | Differentiated (Moderately) | Undifferentiated | Differentiated (Moderately) |
| 12. C − β-glycerophosphate) | Undifferentiated | Undifferentiated | Undifferentiated | Undifferentiated | Undifferentiated |
| 13. C − PA − PC | Undifferentiated | Differentiated (Low) | Differentiated (Low) | Undifferentiated | Undifferentiated |
| 14. C − CD | Differentiated (Highly) | Differentiated (Highly) | Differentiated (Highly) | Differentiated (Highly) | Differentiated (Highly) |
| 15. C − LiCl | Differentiated (Highly) | Differentiated (Highly) | Differentiated (Highly) | Undifferentiated | Differentiated (Highly) |
| 16. C − ITS | Differentiated (Highly) | Differentiated (Highly) | Differentiated (Moderately) | Undifferentiated | Differentiated (Highly) |
| 17. C − CD − LiCl | Differentiated (Highly) | Differentiated (Highly) | Differentiated (Highly) | Differentiated (Highly) | Differentiated (Highly) |
| 18. C − CD − LiCl − VC + (PDGF-BB) | Differentiated (Highly) | Differentiated (Highly) | Differentiated (Highly) | Differentiated (Highly) | Differentiated (Highly) |

In a case where the 10% FBS-bone differentiation-inducing culture medium was used, the mesenchymal stem cells were in an undifferentiated state on the seventh day of the culture as in the case of the result obtained in Example 1 (see Tables 4 through 6). However, low differentiation into osteoblast cells was observed on the fourteenth day of the culture. Further, differentiation was more advanced on the twenty-first day of the culture. In a case where a bone differentiation-inducing culture medium (D:M=1:1) containing 10% FBS was used, a result substantially similar to this result was obtained.

In contrast, in a case where the "serum-free bone differentiation-inducing culture medium: B", i.e., the culture medium prepared by removing EGF, TGF-$\beta_3$, HGF, FGF-2, and PDGF-BB from the culture medium prepared by adding 10 mM of β-glycerophosphate to the STK0 culture medium was used, no differentiation into osteoblast cells was observed even on the twenty-first day after the beginning of differentiation induction. This revealed that in order to carry out bone differentiation induction under a serum-free condition, it is essential to add some growth factor to a culture medium.

The results obtained by carrying out differentiation induction by use of the culture media 4 through 9 in Tables 4 through 6 show which growth factor needs to be added. In a case where TGF-$\beta_3$ or HGF was added to the serum-free bone differentiation-inducing culture medium: B, no differentiation into osteoblast cells was observed even on the twenty-first day after the beginning of differentiation induction as shown in Table 6. In contrast, in a case where EGF or PDGF-BB was added alone to the serum-free bone differentiation-inducing culture medium: B, low differentiation was already observed on the seventh day after the beginning of differentiation induction and was more noticeable than on the fourteenth day of the culture carried out by use of the bone differentiation-inducing culture medium containing 10% FBS. This revealed that some growth factors such as EGF and PDGF-BB are suitable to cause mesenchymal stem cells to differentiate into osteoblast cells with high efficiency and other growth factors such as TGF-$\beta_3$ and HGF are unsuitable to cause mesenchymal stem cells to differentiate into osteoblast cells.

In a case where FGF-2 was added alone to the serum-free bone differentiation-inducing culture medium: B, differentiation into osteoblast cells was induced at lower efficiency as compared to the case where EGF or PDGF-BB was added alone to the serum-free bone differentiation-inducing culture medium: B, and only the cell line G was induced to differentiate into osteoblast cells. However, it became clear that, in a case where the serum-free bone differentiation-inducing culture medium: C, i.e., the culture medium prepared by adding FGF-2 and EGF to the serum-free bone differentiation-inducing culture medium: B was used, differentiation was induced with higher efficiency in the cell line H as compared to the case where EGF was added alone to the serum-free bone differentiation-inducing culture medium: B. This revealed that, in the case where (i) PDGF-BB was added alone to the serum-free bone differentiation-inducing culture medium: B, (ii) EGF was added alone to the serum-free bone differentiation-inducing culture medium: B, or (iii) FGF-2 and EGF were added in combination to the serum-free bone differentiation-inducing culture medium: B, differentiation into osteoblast cells was induced under a serum-free condition with high efficiency.

Further, the results obtained by carrying out differentiation induction by use of the culture media 9 through 18 in Tables 4 through 6 revealed that in order to induce differentiation into osteoblast cells, another factor in addition to the growth factor needs to be added to the serum-free bone differentiation-inducing culture medium: C. In a case where differentiation induction was carried out by use of the culture media 11 and 14 through 16, i.e., even in a case where any one of factors of L-ascorbic acid 2-phosphate sesquimagnesium salt, the lipid concentrate, ITS, and lithium chloride was not added to the serum-free bone differentiation-inducing culture medium: C, low differentiation into osteoblast cells was observed on the seventh day after the beginning of differentiation induction (see Table 4). In addition, according to the results obtained by carrying out differentiation induction by use of the culture media 17 and 18, low differentiation into osteoblast cells was observed on the seventh day after the beginning of differentiation induction also in a case where the factors of L-ascorbic acid 2-phosphate sesquimagnesium salt, the lipid concentrate, ITS, and lithium chloride were not concurrently added to the serum-free bone differentiation-inducing culture medium: C. This revealed that L-ascorbic acid 2-phosphate sesquimagnesium salt, the lipid concentrate, ITS, and lithium chloride are not necessarily essential to induction of differentiation into osteoblast cells under a serum-free condition. The results of Example 2 also revealed that ITS and ascorbic acid, which have been considered to be essential factors for induction of differentiation into osteoblast cells, are not necessarily needed. Therefore, according to the present invention, it is possible to provide a bone differentiation-inducing culture medium additive at a lower price since ITS and ascorbic acid do not need to be added thereto.

Further, in a case where the "C–CD" culture medium, i.e., the culture medium prepared by removing the lipid concentrate from the serum-free bone differentiation-inducing culture medium: C was used, differentiation into osteoblast cells was further promoted as compared to a case where the serum-free bone differentiation-inducing culture medium: C was used. This revealed that a fatty acid had an inhibitory influence on differentiation into osteoblast cells.

In contrast, removal of either one of dexamethasone and β-glycerophosphate from the serum-free bone differentiation-inducing culture medium: C induced no differentiation into osteoblast cells. This revealed that dexamethasone and β-glycerophosphate were essential to the serum-free bone differentiation-inducing culture medium.

Further, in a case where the "C–PA–PC" culture medium, i.e., the culture medium prepared by removing the phospholipids (phosphatidylcholine and phosphatidic acid salt) from the serum-free bone differentiation-inducing culture medium: C was used, differentiation into osteoblast cells was carried out at lower efficiency as compared to the case where the serum-free bone differentiation-inducing culture medium: C was used. This revealed that, in a case where phospholipids were added to the serum-free bone differentiation-inducing culture medium, differentiation into osteoblast cells were further promoted.

As described earlier, FIGS. 1 through 3 and Tables 3 through 6 revealed that, in a case where a serum-free culture medium contained a suitable growth factor and a chemical compound, the mesenchymal stem sells were more highly induced to differentiate into osteoblast cells as compared to a case where the mesenchymal stem sells were cultured by use of a culture medium containing serum in high concentration.

The results of the Examples revealed that the mesenchymal stem sells can be induced to differentiate into osteoblast cells under a serum-free condition in a case where a serum-free culture medium at least contains at least one growth factor selected from the group consisting of EGF, FGF, and PDGF, dexamethasone, and β-glycerophosphate. The results of the Examples also revealed that, in a case where the serum-free culture medium further contains at least one phospholipid in addition to the at least one growth factor, dexamethasone, and β-glycerophosphate, differentiation into osteoblast cells is further promoted. According to this, in a case where at least one growth factor selected from the group consisting of EGF, FGF, and PDGF, dexamethasone, and β-glycerophosphate are added to a basal medium, mesenchymal stem sells can be induced to differentiate into osteoblast cells under a serum-free condition. Also, in a case where at least one phospholipid is further added to the basal medium, differentiation into osteoblast cells can be induced with higher efficiency. Note that Table 7 shows an example of a suitable composition of a serum-free culture medium. In the present description, a serum-free culture medium having the composition shown in Table 7 is hereinafter referred to as an "STK3 culture medium".

TABLE 7

| | Source | Effective concentration | Optimum concentration |
| --- | --- | --- | --- |
| Basal culture medium | | | |
| α-MEM/MCDB201 | Sigma: M4526/M6770 Supplement A (Basal factor) | 1:1 | |
| Dexamethasone (Dex) | Sigma: D1756 | $10^{-6}$-$10^{-10}$ M | $10^{-8}$ M |
| β-glycerophosphate | Tokyo Chemical Industry: G0195 | 1-100 mM | 10 mM |

TABLE 7-continued

| | Source | Effective concentration | Optimum concentration |
|---|---|---|---|
| Ascobic acid 2-phosphate sesquimagnesium salt (VC) | Sigma: A8960 | 0.5-200 µg/ml | 50 µg/ml |
| (human recombinant) Insulin | Wako: 090-03446 | 0.5-50 µg/ml | 10 µg/ml |
| Transferrin | Sigma: T0665 | 0.5-50 µg/ml | 5.5 µg/ml |
| Selenous acid | Sigma: 211176 | 0.5-50 ng/ml | 6.7 ng/ml |
| Human serum albumin (HSA) | Sigma: A1887 | 0.1-50 mg/ml | 1.25 mg/ml |
| Supplement B (Phospholipid) | | | |
| Phosphatidylcholine (PC) | Wako: 163-21181 | (Total amount 0.1-30 µg/ml) | 5 µg/ml |
| Phosphatidic acid sodium salt (PA) | Sigma: P9511 | | 5 µg/ml |
| Supplement D (Growth factor) | | | |
| (human recombinant) Basic fibroblast growth factor (bFGF) | Kaken Pharmaceutical: KCB-1 | 0.1-100 ng/ml | 1 ng/ml |
| (human recombinant) Epidermal growth factor (EGF) | Wako: 050-07141 | 0.5-200 ng/ml | 20 ng/ml |
| (human recombinant) Platelet derived growth factor (PDGF-BB) | Wako: 160-19741 | 0.5-100 ng/ml | 10 ng/ml |
| Others | | | |
| L-Glutathione (reduced) | Sigma: G6013 | 0.1-10 µg/ml | 2 µg/ml |

Example 3

Study on Differentiation of Mesenchymal Stem Cells into Osteoblast Cells (3)

Three human ilium-marrow-derived mesenchymal stem cell lines (hereinafter referred to as a cell line K, a cell line L, and a cell line M) (purchased from Bio-Whittaker Inc. (Walkersville, Md.)) were used as mesenchymal stem cells. Note that the cell line K is an eighth subculture of human ilium-marrow-derived mesenchymal stem cells, the cell line L is a seventh subculture of human ilium-marrow-derived mesenchymal stem cells and the cell line M is a tenth subculture of human ilium-marrow-derived mesenchymal stem cells.

(1. Induction of Bone Differentiation of Mesenchymal Stem Cells Proliferated and Cultured by Use of Serum-Free STK2 Culture Medium)

The mesenchymal stem cells were seeded on a 6-well microplate containing a serum-free STK2 culture medium at a density of 5000 cells/cm$^2$. Culture media were replaced every two or three days during the cell culture.

The mesenchymal stem cells were washed two times with PBS before becoming confluent. Then, the mesenchymal stem cells were incubated for two minutes in PBS containing 0.05% trypsin and 0.2 mM EDTA, so that the mesenchymal stem cells were detached from the microplate. Then, the mesenchymal stem cells were re-suspended with a plant-derived trypsin inhibitor (Produced by Sigma Aldrich, Inc.: T6522) that contained no serum.

Subsequently, the mesenchymal stem cells were washed three times with the serum-free STK2 culture medium. Then, the mesenchymal stem cells were seeded on a 24-well microplate at a density of 5000 cells/cm$^2$ in such a manner that the mesenchymal stem cells per cell line were seeded on three (n=3) wells for each condition. The mesenchymal stem cells were cultured in the serum-free STK2 culture medium at 37° C. in a CO$_2$ incubator with 5% CO$_2$ until becoming confluent.

The 24-well microplate to which bottom surface the mesenchymal stem cells in a confluent state were attached was washed two to three times with a serum-free DMEM culture medium. Differentiation-culture was carried out by use of a 10% FBS-bone differentiation-inducing culture medium or a serum-free bone differentiation-inducing culture medium (STK3 culture medium). As described in Example 1, the "10% FBS-bone differentiation-inducing culture medium" was prepared by adding, to α-MEM, FBS in a final concentration of 10% by weight, dexamethasone in a final concentration of 100 nM, β-glycerophosphate in a final concentration of 10 mM, and L-ascorbic acid 2-phosphate sesquimagnesium salt in a final concentration of 50 µg/ml. The "10% FBS-bone differentiation-inducing culture medium" is identical to a conventionally publicly-known bone differentiation-inducing culture medium used in Patent Literature 1. An old culture medium was replaced with an identical new one every two or three days during differentiation induction. On the fourth, seventh, fourteenth, or twenty-first day of the culture for differentiation in the respective culture media, evaluation of differentiation into osteoblast cells was carried out by staining the mesenchymal stem cells with alizarin red. FIG. 4 and Tables 8 through 11 show results.

(2. Induction of Bone Differentiation of Mesenchymal Stem Cells Proliferated and Cultured by Use of DMEM Culture Medium Containing 10% FBS)

The mesenchymal stem cells were seeded on a 6-well microplate containing a DMEM culture medium containing 10% FBS at a density of 5000 cells/cm$^2$. Culture media were replaced every two or three days during the cell culture.

The mesenchymal stem cells were washed two times with PBS before becoming confluent. Then, the mesenchymal stem cells were incubated for two minutes in PBS containing 0.05% trypsin and 0.2 mM EDTA, so that the mesenchymal stem cells were detached from the microplate. Then, the mesenchymal stem cells were re-suspended with a plant-derived trypsin inhibitor (Produced by Sigma Aldrich, Inc.: T6522) that contained no serum.

Subsequently, the mesenchymal stem cells were seeded on a 24-well microplate containing the DMEM culture medium containing 10% FBS at a density of 5000 cells/cm$^2$ in such a manner that the mesenchymal stem cells per cell line were seeded on three (n=3) wells for each condition. The mesenchymal stem cells were cultured at 37° C. in a CO$_2$ incubator with 5% CO$_2$ until becoming confluent.

The 24-well microplate to which bottom surface the mesenchymal stem cells in a confluent state were attached was washed two to three times with a serum-free DMEM culture medium. Differentiation-culture was carried out by use of a 10% FBS-bone differentiation-inducing culture medium or a serum-free bone differentiation-inducing culture medium (STK3 culture medium). An old culture medium was replaced with an identical new one every two or three days during differentiation induction. On the fourth, seventh, fourteenth, or twenty-first day of the culture for differentiation in the respective culture media, evaluation of differentiation into osteoblast cells was carried out by staining the mesenchymal stem cells with alizarin red. FIG. 4 and Tables 8 through 11 show results.

TABLE 8

| Differentiation Culture medium type/Cell line | Result of bone differentiation 4th day | | | | | |
|---|---|---|---|---|---|---|
| | Cell proliferated and cultured by use of DMEM culture medium containing 10% FBS | | | Cell proliferated and cultured by use of serum-free proliferation culture medium (STK2 culture medium) | | |
| | Cell line K | Cell line L | Cell line M | Cell line K | Cell line L | Cell line M |
| 10% FBS-bone differentiation-inducing culture medium | Undifferentiated | Undifferentiated | Undifferentiated | Undifferentiated | Undifferentiated | Undifferentiated |
| Serum-free bone differentiation-inducing culture medium (STK3 culture medium) | Undifferentiated | Undifferentiated | Undifferentiated | Differentiated (Low) | Differentiated (Low) | Differentiated (Low) |

TABLE 9

| Differentiation Culture medium type/Cell line | Result of bone differentiation 7th day | | | | | |
|---|---|---|---|---|---|---|
| | Cell proliferated and cultured by use of DMEM culture medium containing 10% FBS | | | Cell proliferated and cultured by use of serum-free proliferation culture medium (STK2 culture medium) | | |
| | Cell line K | Cell line L | Cell line M | Cell line K | Cell line L | Cell line M |
| 10% FBS-bone differentiation-inducing culture medium | Undifferentiated | Undifferentiated | Undifferentiated | Undifferentiated | Differentiated (Low) | Differentiated (Low) |
| Serum-free bone differentiation-inducing culture medium (STK3 culture medium) | Differentiated (Low) | Differentiated (Low) | Differentiated (Low) | Differentiated (Moderately) | Differentiated (Moderately) | Differentiated (Moderately) |

TABLE 10

| Differentiation Culture medium type/Cell line | Result of bone differentiation 14th day | | | | | |
|---|---|---|---|---|---|---|
| | Cell proliferated and cultured by use of DMEM culture medium containing 10% FBS | | | Cell proliferated and cultured by use of serum-free proliferation culture medium (STK2 culture medium) | | |
| | Cell line K | Cell line L | Cell line M | Cell line K | Cell line L | Cell line M |
| 10% FBS-bone differentiation-inducing culture medium | Differentiated (Low) | Differentiated (Low) | Differentiated (Low) | Differentiated (Low) | Differentiated (Low) | Differentiated (Low) |
| Serum-free bone differentiation-inducing culture medium (STK3 culture medium) | Differentiated (Moderately) | Differentiated (Moderately) | Differentiated (Moderately) | Differentiated (Highly) | Differentiated (Highly) | Differentiated (Highly) |

TABLE 11

| Differentiation Culture medium type/Cell line | Result of bone differentiation 21st day | | | | | |
|---|---|---|---|---|---|---|
| | Cell proliferated and cultured by use of DMEM culture medium containing 10% FBS | | | Cell proliferated and cultured by use of serum-free proliferation culture medium (STK2 culture medium) | | |
| | Cell line K | Cell line L | Cell line M | Cell line K | Cell line L | Cell line M |
| 10% FBS-bone differentiation-inducing culture medium | Differentiated (Low) | Differentiated (Low) | Differentiated (Low) | Differentiated (Moderately) | Differentiated (Moderately) | Differentiated (Moderately) |

TABLE 11-continued

| Differentiation | Result of bone differentiation 21st day | | | | | |
|---|---|---|---|---|---|---|
| Culture medium type/ | Cell proliferated and cultured by use of DMEM culture medium containing 10% FBS | | | Cell proliferated and cultured by use of serum-free proliferation culture medium (STK2 culture medium) | | |
| Cell line | Cell line K | Cell line L | Cell line M | Cell line K | Cell line L | Cell line M |
| Serum-free bone differentiation-inducing culture medium (STK3 culture medium) | Differentiated (Highly) | Differentiated (Highly) | Differentiated (Highly) | Differentiated (Highly) | Differentiated (Highly) | Differentiated (Highly) |

FIG. 4 shows a result of induction of differentiation of the mesenchymal stem cells into osteoblast cells. Table 8 shows a result of bone differentiation which result was obtained on the fourth day after the beginning of differentiation induction. Table 9 shows a result of bone differentiation which result was obtained on the seventh day after the beginning of differentiation induction. Table 10 shows a result of bone differentiation which result was obtained on the fourteenth day after the beginning of differentiation induction. Table 11 shows a result of bone differentiation which result was obtained on the twenty-first day after the beginning of differentiation induction. The mesenchymal stem cells proliferated and cultured by use of the serum-free STK2 culture medium and differentiation-induced by use of the serum-free STK3 culture medium were already differentiating into osteoblast cells on the fourth day after the beginning of bone differentiation induction (see FIG. 4 and Table 8).

In contrast, the mesenchymal stem cells proliferated and cultured by use of the STK2 culture medium and differentiation-induced by use of the (conventional) 10% FBS-bone differentiation-inducing culture medium were in an undifferentiated state. Each of (i) the mesenchymal stem cells proliferated and cultured by use of the DMEM culture medium containing 10% FBS and differentiation-induced by use of the serum-free STK3 culture medium and (ii) the mesenchymal stem cells proliferated and cultured by use of the DMEM culture medium containing 10% FBS and differentiation-induced by use of the 10% FBS-bone differentiation-inducing culture medium were in the undifferentiated state.

Each of (i) the mesenchymal stem cells proliferated and cultured by use of the DMEM culture medium containing 10% FBS and differentiation-induced by use of the serum-free STK3 culture medium and (ii) the mesenchymal stem cells proliferated and cultured by use of the serum-free STK2 culture medium and differentiation-induced by use of the serum-free STK3 culture medium were already differentiating into osteoblast cells on the seventh day after the beginning of bone differentiation induction (see FIG. 4 and Table 9).

The mesenchymal stem cells proliferated and cultured by use of the serum-free STK2 culture medium and differentiation-induced by use of the serum-free STK3 culture medium were slightly higher in degree of differentiation into osteoblast cells than the mesenchymal stem cells proliferated and cultured by use of the DMEM culture medium containing 10% FBS and differentiation-induced by use of the serum-free STK3 culture medium.

In contrast, the mesenchymal stem cells proliferated and cultured by use of the DMEM culture medium containing 10% FBS and differentiation-induced by use of the 10% FBS-bone differentiation-inducing culture medium were in the undifferentiated state.

The mesenchymal stem cells proliferated and cultured by use of the DMEM culture medium containing 10% FBS and differentiation-induced by use of the 10% FBS-bone differentiation-inducing culture medium were already differentiating into osteoblast cells on the fourteenth day after the beginning of bone differentiation induction (see FIG. 4 and Table 10).

However, the mesenchymal stem cells proliferated and cultured by use of the DMEM culture medium containing 10% FBS and differentiation-induced by use of the 10% FBS-bone differentiation-inducing culture medium were lower in degree of differentiation into osteoblast cells than the mesenchymal stem cells proliferated and cultured by use of the DMEM culture medium containing 10% FBS and differentiation-induced by use of the serum-free STK3 culture medium.

In contrast, the mesenchymal stem cells proliferated and cultured by use of the serum-free STK2 culture medium and differentiation-induced by use of the serum-free STK3 culture medium were higher in degree of differentiation into osteoblast cells than the mesenchymal stem cells proliferated and cultured by use of the DMEM culture medium containing 10% FBS and differentiation-induced by use of the serum-free STK3 culture medium.

Each of (i) the mesenchymal stem cells proliferated and cultured by use of the DMEM culture medium containing 10% FBS and differentiation-induced by use of the serum-free STK3 culture medium and (ii) the mesenchymal stem cells proliferated and cultured by use of the serum-free STK2 culture medium and differentiation-induced by use of the serum-free STK3 culture medium was high in degree of differentiation into osteoblast cells on the twenty-first day after the beginning of bone differentiation induction (see FIG. 4 and Table 11).

In contrast, the mesenchymal stem cells proliferated and cultured by use of the DMEM culture medium containing 10% FBS and differentiation-induced by use of the 10% FBS-bone differentiation-inducing culture medium were lower in degree of differentiation into osteoblast cells than the mesenchymal stem cells proliferated and cultured by use of the serum-free STK2 culture medium and differentiation-induced by use of the 10% FBS-bone differentiation-inducing culture medium.

The results of Example 3 revealed that in the case where the serum-free STK3 culture medium was used, the mesenchymal stem cells could be differentiated into osteoblast cells with higher efficiency and in a shorter period than in the case where the conventional 10% FBS-bone differentiation-inducing culture medium was used. This revealed that the mesenchymal stem cells proliferated and cultured by use of the serum-free STK2 culture medium maintained a higher potential for differentiating into osteoblast cells than the mesenchymal stem cells proliferated and cultured by use of the DMEM culture medium containing 10% FBS.

In a case where a conventional 10% FBS-bone differentiation-inducing culture medium is used, it takes two to three weeks for mesenchymal stem cells to differentiate into osteoblast cells. In contrast, the results of Example 3 show that the mesenchymal stem cells proliferated and cultured by use of the serum-free STK2 culture medium and differentiation-induced by use of the serum-free STK3 culture medium were already differentiating into osteoblast cells on the fourth day after the beginning of bone differentiation induction. It can be hypothesized that this is because use of the serum-free STK2 culture medium and the serum-free STK3 culture medium in combination synergistically promoted induction of differentiation of the mesenchymal stem cells into osteoblast cells.

INDUSTRIAL APPLICABILITY

A serum-free culture medium to which a differentiation-inducing culture medium additive of the present invention for inducing bone differentiation of at least one type of cell selected from the group consisting of a stem cell, a dental pulp cell, a periodontal ligament cell, a placenta, an amnion, and a fibroblast under a serum-free condition is added allows higher degree of bone differentiation of the at least one type of cell selected from the group consisting of a stem cell, a dental pulp cell, a periodontal ligament cell, a placenta, an amnion, and a fibroblast than a conventional differentiation-inducing culture medium containing a serum. Therefore, the differentiation-inducing culture medium additive is suitably usable for regenerative medicine, for example.

The invention claimed is:

1. A culture method for inducing bone differentiation of mesenchymal stem cells under a serum-free condition, the culture method comprising the step of:
   differentiating cells of a mesenchymal stem cell line in a culture medium within fourteen days,
   the culture medium comprising:
   PDGF and at least one growth factor selected from the group consisting of EGF and FGF;
   dexamethasone;
   β-glycerophosphate; and
   a basal medium,
   the culture medium containing no serum and further does not contain TGF-β or HGF.

2. The culture method according to claim 1, wherein the culture medium further contains at least one phospholipid.

3. The culture method according to claim 2, wherein the at least one phospholipid is selected from the group consisting of phosphatidic acid, lysophosphatidic acid, phosphatidylinositol, phosphatidylserine, phosphatidylethanolamine, phosphatidyl choline, and phosphatidylglycerol.

4. The culture method according to claim 2, wherein the culture medium further contains an oxidation inhibitor.

5. The culture method according to claim 4, wherein the oxidation inhibitor is DL-α-tocopherol acetate (vitamin E).

6. The culture method according to claim 1, further comprising the step of:
   proliferating at least one type of cell selected from the group consisting of the stem cell, the dental pulp cell, the periodontal ligament cell, the placenta, the amnion, and the fibroblast in a serum-free culture medium containing at least three growth factors selected from the group consisting of FGF, PDGF, EGF, TGF-β, and HGF and at least one phospholipid before the step of differentiating.

* * * * *